United States Patent [19]

Gimbrone, Jr. et al.

[11] Patent Number: 5,451,399

[45] Date of Patent: Sep. 19, 1995

[54] [ALA IL-8]$_{77}$ AND [SER IL-8]$_{72}$ AS LEUKOCYTE ADHESION INHIBITORS

[75] Inventors: Michael A. Gimbrone, Jr., Jamaica Plain; Martin S. Obin, Newton Centre, both of Mass.; Joffre B. Baker, El Granada; Caroline A. Hebert, San Francisco, both of Calif.

[73] Assignees: Brigham and Women's Hospital, Boston, Mass.; Genentech, Inc., South San Francisco, Calif.

[21] Appl. No.: 964,525

[22] Filed: Oct. 19, 1992

Related U.S. Application Data

[62] Division of Ser. No. 443,131, Nov. 29, 1989, abandoned.

[51] Int. Cl.$^6$ .............. A61K 45/05; A61K 37/00; A61K 37/10; C07K 13/00
[52] U.S. Cl. .................. 424/85.2; 514/886; 514/2; 514/8; 514/12; 530/351
[58] Field of Search ............ 424/85.1, 85.2; 514/2, 514/8, 12, 21, 886

[56] References Cited

U.S. PATENT DOCUMENTS

| | | | |
|---|---|---|---|
| 4,897,348 | 1/1990 | Johnson et al. | 435/69.1 |
| 5,302,384 | 4/1994 | Gimbrone et al. | 424/85.2 |
| 5,306,627 | 4/1994 | Yamada et al. | 435/69.5 |

OTHER PUBLICATIONS

BACHEM Biosciences Inc., Lymphokine Bulletin Information Sheet, Feb. 1991 (BA 054).
Baggiolini et la., Neutrophil-activating Peptide-1/Interleukin 8, a Novel Cytokine That Activates Neutrophils, J. Clin. Invest. 84:1045–1049 (Oct., 1989).
Clore et al., Determination of the Secondary Structure of Interleukin-8 by Nuclear Magnetic Resonance Spectroscopy, J. Biol. Chem. 264(32):18907–18911 (Nov. 15, 1989).
Dahinden et al., The Neutrophil-Activating Peptide NAF/NAP-1 Induces Histamine and Leukotriene Release By Interleukin 3-Primed Basophils, J. Exp. Med. 170:1787–1792 (Nov., 1989).
Dixit et al., Molecular Cloning of an Endotheilial Derived Neutrophil Chemotactic Factor: Identity with Monocyte Derived Factor, EMBO J. 3:A305, abstract 456 (1989).
Furata et al., Production and Characterization of Recombinant Human Neutrophil Chemotactic Factor, J. Biochem. 106:436–441 (1989).
Gimbrone et al., Endothelial Interleukin-8: A Novel Inhibitor of Leukocyte-Endothelial Interactions, Science 246:1601–1603 (Dec., 1989).
Gregory et al., Structure Determination of a Human Lymphocyte Derived Neutrophil Activating Peptide (LYNAP), Biochem. and Biophys. Res. Comm. 151(2):883–890 (Mar. 15, 1988).
Hechtman et al., Inhibitor of Polymorphonuclear Leukocyte Accumulation at Sites of acute Inflammation, J. Immunol. 147(3):883–892 (Aug. 1, 1991).
Hébert et al., Endothelial and Leukocyte Forms of IL-8, Conversion by Thrombin and Interactions with Neutrophils, Journal of Immunology 145(9):3033–3040 (Nov. 1, 1990).
Kowalski et al., Regulation of the mRNA for Monocyte-Derived Neutrophil-Activating Peptide in Differentiating HL60 Promyelocytes, Molec. and Cell. Biol. 9(5):1946–1957 (May. 1989).
Larsen et al., Production of interleukin-8 by human dermal fibroblasts and keratinocytes in response to interleukin-1 or tumour necrosis factor, Immunology 68:31–36 (1989).

(List continued on next page.)

Primary Examiner—Garnette D. Draper
Assistant Examiner—K. Cochrane Carlson
Attorney, Agent, or Firm—Sterne, Kessler, Goldstein & Fox

[57] ABSTRACT

A novel polypeptide [Ala IL-8]$_{77}$ is provided which is a potent modulator of neutrophil functions. The polypeptide factor and related compositions find use as anti-inflammatory agents and as therapeutics for clinical indications in which damage to vascular endothelium and other tissues occurs. The amino acid and nucleotide sequence of the factor and methods for its purification, recombinant production and pharmaceutical use are provided.

3 Claims, 16 Drawing Sheets

OTHER PUBLICATIONS

Larsen et al., The Neutrophil [...] Protein (NAP-1) is Also Chemotactis for T Lymphocytes, *Science* 243:1464–1466 (Mar., 1989).

Lee et al., *Isolation and Characterization of Eight Tumor Necrosis Factor–Induced Gene Sequences from Human Fibroblasts*, Mol. Biol. 10:1982–1988 (1990).

Lindley et al., Synthesis and expression *Escherichia coli* of the gene encoding monocyte–derived neutrophpil–activating factor: Biological equivalence between . . ., *PNAS USA* 85:9199–9203 (Dec., 1988).

Matsushima et al., Molecular Cloning of a Human Monocyte–Derived Neutrophil Chemotactic Factor (MDNCF) and the Induction of MDNCF mRNA By Interleukin 1 . . ., *J. Exp. Med.* 167:1883–1893 (Jun. 1988).

Miller et al., Cloning and Expression of a Yeast Ubiquitin–protein Cleaving Activity in *Escherichia coli*, *Bio/Technology* 7:698–704 (Jul., 1989).

Modi et al., Monocyte–derived neutrophil chemotactic factor (MDNCF/IL–8) resides in a gene cluster along with several other members of the platelet factor 4 gene . . ., *Hum. Genet.* 84:185–187 (1990).

Mukaida et al., Genomic Structure of the Human Monocyte–Derived Neutrophil Chemotactic Factor IL–8, *J. Immunol.* 143:1366–1371 (Aug. 15, 1989).

Mullenbach et al., Chemical Synthesis and Expression in Yeat of a Gene Encoding Connective Tissue Activating Peptide–III, *J. Biol. Chem.* 261(2):719–722 (Jan. 15, 1986).

Schmid et al., Induction of mRNA For A Serine Protease And A β–Thromboglobulin–Like Protein in Mitogen–Stimulated Human Leukocytes, *J. Immunol.* 139:250–256 (Jul. 1, 1987).

Schröder et al., Secretion of Novel and Homologous Neutrophil–Activating Peptides by LPS–Stimulated Human Endothelial Cells, *J. Immunol.* 142:244–251 (Jan. 1, 1989).

Schröder, J. M., The Monocyte–Derived Neutrophil Activating Peptide (NAP/Interleukin 8) Stimulates Human Neutrophil Arachidonate-5-Lipoxygenase, But Not . . ., *J. Exp. Med.* 170:847–863 (Sep., 1989).

Schröder et al., Purification and Partial Biochemical Characterization of a Human Monocyte–Derived, Neutrophil–Activation Peptide That Lacks Inter–. . ., *J. Immunol.* 139(10):3474–3483 (Nov. 15, 1987).

Strieter et al., Endothelial Cell Gene Expression of a Neutrophil Chemotactic Factor by TNF–α, LPS, and IL–1β, *Science* 243:1467–1469 (Mar. 17, 1989).

Suzuki et al., Localization of chemotactic activity and 64 kD protein phosphorylation for human polymorphonuclear leukocytes in . . ., *Biochem. and Biophys. Res. Comm.* 163:1298–1305 (Sep. 29, 1989).

Suzuki et al., Purification and Partial Primary Sequence of a Chemotactic Protein For Polymorphonuclear Leukocytes Derived From Human Lung Giant Cell Carcinoma . . ., *J. Exp. Med.* 169:1895–1901 (Jun., 1989).

Van Damme et al., The chemotactic activity for granulocytes produced by virally infected fibroblasts is identical to monocyte–derived interleukin 8, *Eur. J. Immunol.* 19:1189–1194 (1989).

Van Damme et al., Purification of granulocyte chemotactic peptide/interleukin–8 reveals N–terminal sequence heterogeneity similar to that of β–thromboglobulin, *Eur. J. Biochem.* 181:337–344 (1989).

Van Damme et al., A Novel, $NH_2$–Terminal Sequence–Characterized Human Monokine Possessing Neutrophil Chemotactic, Skin–Reactive, and Granulocytosis–Promoting . . ., *J. Exp. Med.* 167:1364–1376 (Apr., 1988).

Wheeler et al., Cultured Human Endothelial Cells Stimulated with Cytokines or Endotoxin Produce an Inhibitor of Leukocyte Adhesion, *J. Clin. Invest.* 82:1211–1218 (Oct., 1988).

Wheeler et al., Characterization of an Endothelial–Derived Inhibitor of Leukocyte Adhesion, *Fed. Proc.* 46:758, Abstract No. 2577 (1987).

Wheeler et al., Interleukin–1 Treated endothelial Cells Produce an Inhibitor of Leukocyte–Endothelial Adhesion, *Fed. Proc.* 46:450, Abstract No. 1725 (1986).

Willems et al., Human granulocyte chemotactic peptide (IL–8) as a specific neutrophil degranulator: comparison with other monokines, Immunol. 67:540–542 (1989).

Yoshimura et al., Neutrophil Chemotactic Factor Produced By Lipopolysaccharide (LPS)–Stimulated Human Blood Mononuclear Leukocytes: Partial Character . . ., *J. Immunol.* 139(3):788–793 (Aug. 1, 1987).

Yoshimura et al., Purification of a human monocyte–derived neutrophil chemotactic factor that has peptide sequence similarity to other host defense cytokins, *PNAS USA* 84:9233–9237 (Dec., 1987).

Yoshimura et al., Three forms of monocyte–derived neutrophil chemotactic Factor (MDNCF) distinguished by Different Lenths of the Amino–Terminal Sequence, *Molecular Immunology* 26(1):87–93 (1989).

```
ATG ACT TCC AAG CTG GCC GTG GCT CTC TTG CGA GCC TTC CTG ATT
 M   T   S   K   L   A   V   A   L   L   R   A   F   L   I

TCT GCA GCT CTG TGT GAA GGT GCA GTT TTG CCA AGG AGT GCT AAA
 S   A   A   L   C   E   G * A   V   L   P   R↓S   A   K

GAA CTT AGA TGT CAG TGC ATA AAG ACA TAC TCC AAA CCT TTC CAC
 E   L   R   C   Q   C   I   K   T   Y   S   K   P   F   H

CCC AAA TTT ATC AAA GAA CTG AGA GTG ATT GAG AGT GGA CCA CAC
 P   K   F   I   K   E   L   R   V   I   E   S   G   P   H

TGC GCC AAC ACA GAA ATT ATT GTA AAG CTT TCT GAT GGA AGA GAG
 C   A   N   T   E   I   I   V   K   L   S   D   G   R   E

CTC TGT CTG GAC CCC AAG GAA AAC TGG GTG CAG AGG GTT GTG GAG
 L   C   L   D   P   K   E   N   W   V   Q   R   V   V   E

AAG TTT TTG AAG AGG GCT GAG AAT TCA
 K   F   L   K   R   A   E   N   S
```

FIG. 1

[ALA IL-8]$_{77}$ AND [SER IL-8]$_{72}$ AS LEUKOCYTE ADHESION INHIBITORS

This application is a division, of application Ser. No. 07/443,131, filed Nov. 29, 1989, now abandoned.

FIELD OF THE INVENTION

The present invention is drawn to the isolation and characterization of polypeptides which serve as leukocyte adhesion inhibitors, and their use as anti-inflammatory agents and as therapeutics for clinical indications in which leukocyte-mediated damage of vascular endothelium and/or underlying tissue occurs.

BACKGROUND OF THE INVENTION

Vascular endothelial cells participate in acute and inflammatory reactions. A marked feature of this reaction is a selective early influx of neutrophils from the peripheral blood. Circulating and bone marrow neutrophils provide a front line of defense that is rapidly mobilized and activated against infectious agents.

When foreign invaders such as bacteria, viruses or other invading parasites penetrate the skin or mucous membranes, an inflammatory response is mounted. This is characterized by dilation of surrounding blood vessels, an increase in vascular permeability, and the migration of monocytes and neutrophils across vascular walls. The first step in extravasation involves adhesive interactions of leukocytes with the vascular endothelium, which must be regulated to allow localization of leukocytes only at inflammatory sites.

Recent studies have demonstrated that certain inflammatory cytokines such as interleukin-1 (IL-1), tumor necrosis factor (TNF), and gram-negative bacterial endotoxin (lipopolysaccharide) can act directly on vascular endothelium in vitro to increase the adhesiveness of the endothelial blood cells for blood leukocytes as well as related leukocyte cell lines (HL-60 and U937). Studies of human and animal tissues indicate that a similar process of endothelial activation occurs in various inflammatory disease processes in vivo.

After attachment to endothelial cells or other cells, neutrophils may exert damaging effects through several mechanisms. Upon stimulation, neutrophils generate and release toxic oxygen metabolites, numerous proteases, and phospholipase products, all of which may result in vasomotor changes, endothelial injury and loss of vascular integrity. Increased neutrophil adhesiveness is a critical, early step in the sequence of events leading to neutrophil-mediated injury. Increased adhesiveness results in neutrophil adhesion to endothelium or other cells and/or neutrophil aggregation.

Therefore, the inhibition of leukocyte adhesion potentially is of central importance in therapeutic interventions in inflammatory disease processes. While leukocyte adhesion is normally desirable, it is also implicated in immune and nonimmune disease processes, including organ transplant rejection, tissue graft rejection, allergic reactions, autoimmune diseases, rheumatoid arthritis, septic shock, adult respiratory distress syndrome (ARDS), glomerulonephritis, and other tissue or organ-specific forms of acute and chronic inflammation. Further, in the setting of ischemia-reperfusion, leukocyte adhesion may produce microvascular occlusion, tissue injury and death.

The present invention is drawn to compositions which are potent modulators of neutrophil functions. These compositions have important anti-inflammatory properties which support their use as protective agents in neutrophil-mediated endothelial and other tissue injury.

Description of the Related Art

An excellent review of the defense system is provided by Isen, H. W., N; *Microbiology*, 3rd edition, Harper & Row, Philadelphia, Pa. (1980), pp. 290–295 and 381–418.

Schmid and Weissman, *J. Immunol* 139:250 (1987), describe the coding sequence of two cDNA clones corresponding to genes that are induced in peripheral human blood leukocytes by Staphylococcal enterotoxin A.

Streiter et al., *Science* 243:1467 (1989), disclose that human endothelial cells can secrete a neutrophil chemotactic factor (NCF) with molecular and physical characteristics consistent with monocyte-derived NCF.

Varani et al., *Lab. Investigation* 59:292 (1988), show that pretreatment of rat pulmonary artery endothelial cells with tumor necrosis factor is not directly cytotoxic but dramatically increases their susceptibility to killing by activated human neutrophils.

Yoshimura et al., *Proc. Natl. Acad. Sci. USA* 87:9233 (1987), report the purification to homogeneity of a monocyte-derived neutrophil chemotactic factor (MDNCF). MDNCF is released by an inflammatory stimulus and has a selective capacity to attract neutrophils but not monocytes.

Larsen et al., *Science* 243:1464 (1989), report that T lymphocyte chemotactic factor (TCF) appears to be biologically and biochemically identical to a neutrophil-chemotactic factor that is also a neutrophil-activating protein (NAP-1).

A series of papers including several of those listed above describe a polypeptide product from the above gene (3–10C) identified by Schmid and Weissman (e.g., Streiter et al., Yoshimura et al., and Larsen et al.) When the primary structure of the polypeptide product was identified the predominant species was found to be 72 amino acids long, beginning at a serine residue. Other, minor species including an NH$_2$-terminal extended 77 residue form beginning at an alanine residue (herein referred to as [Ala IL-8]$_{77}$) were in several cases shown to be present. Although the 72 amino acid residue was identified by several different names, the term "interleukin 8, (IL-8)" became adopted by a number of investigators (Larsen et al., supra; Shroeder et al., *J. Exp. Med.* 170:847 [1989]; and Baggiolini et al., *J. Clin. Invest.* 84:1045 [1989]).

It is noteworthy that (1) the biological activities of IL-8 identified heretofore all indicated that this polypeptide functions in a proinflammatory capacity and (2) that the longer forms of IL-8 (in particular the above mentioned 77 residue form, [Ala IL-8]$_{77}$) have never been purified nor their activities demonstrated.

SUMMARY OF THE INVENTION

A novel polypeptide [Ala IL-8]$_{77}$ is provided which is a potent modulator of neutrophil functions. The polypeptide is secreted by interleukin-1 (IL-1), tumor necrosis factor (TNF), or bacterial endotoxin (LPS)-activated endothelial cells. The polypeptide factor and related compositions find use as anti-inflammatory agents. The amino acid and nucleotide sequence of the factor and methods for its recombinant production and pharmaceutical use are provided.

DESCRIPTION OF THE FIGURES

FIG. 1 Nucleotide sequence coding for [Ala IL-8]$_{77}$ (beginning at asterisk) and IL-8 (beginning at arrow).

DESCRIPTION OF THE SPECIFIC EMBODIMENTS

The [Ala IL-8]$_{77}$ Polypeptide: Sources, Isolation and Structure

The subject polypeptide is an N-terminal extended form of IL-8 as well as derivatives and analogs thereof. The polypeptide has been designated [Ala IL-8]$_{77}$. This polypeptide has been identified as the major IL-8 species secreted by activated human endothelial cells and is available from such activated cultures. In particular, the cytokines interleukin-1 (IL-1) and tumor necrosis factor (TNF), as well as bacterial endotoxin (LPS), act directly on cultured human endothelial cells (HEC) to induce the expression and secretion of [Ala IL-8]$_{77}$.

Figure 7:
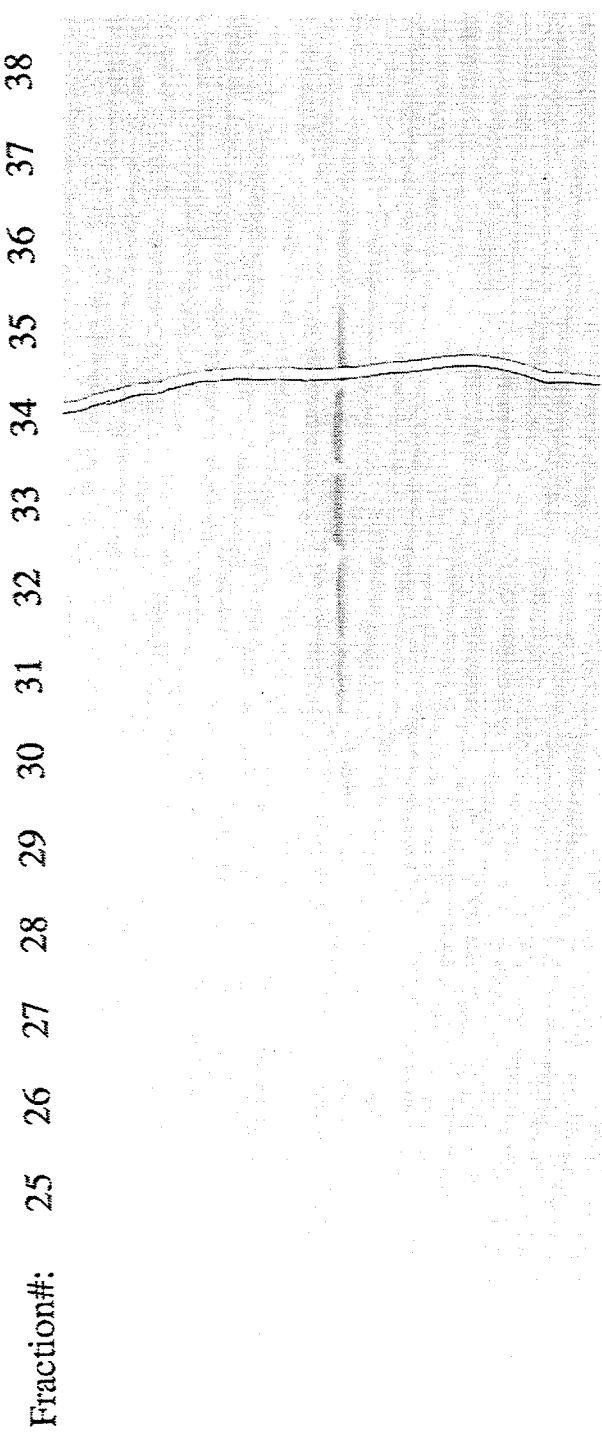
FIG. 7 Chromatographic resolution of [Ala IL-8]$_{77}$ and [Ser IL-8]$_{72}$ on a Mono S cation exchange column. Electrophoresis of nonreduced fractions in Tris/Tricine gel system showing chromatographic resolution of [Ala IL-8]$_{77}$ (peak in fractions 30–37) and [Ser IL-8]$_{72}$ (peak in fractions 27 and 28). (See Example 3.)

For the production of [Ala IL-8]$_{77}$, human endothelial cells may be grown in a nutrient medium and treated with an appropriate inducer. As indicated above, these inducers include IL-1, TNF, LPS, and the like. After treatment with the inducer for a sufficient time, usually 8 to 24 hours, [Ala IL-8]$_{77}$ can be isolated from the HEC conditioned medium by sequential ion exchange and reversed phase high performance liquid chromatography using an inhibition of neutrophil adhesion to activated HEC monolayers (leukocyte adhesion inhibition [LAI]) as the bioassay. The [Ala IL-8]$_{72}$ polypeptide can be separated from [Ser IL-8]$_{72}$ by chromatography (FIG. 7). The ratio of [Ser IL-8]$_{72}$ to [Ala IL-8]$_{77}$ varies depending upon the culture source of the polypeptides as well as the time of incubation. Generally, [Ser IL-8]$_{72}$ is found as a minor component from endothelial cell-derived material comprising from about 5% to about 15%, usually about 7% of [Ser IL-8]$_{72}$/[Ala IL-8]$_{77}$ from 8 hour conditioned medium, and from about 10% to about 30%, usually about 20% from 24 hour conditioned medium. In contrast, from mononuclear leukocyte-derived material, [Ser IL-8]$_{77}$ is found as the predominant form, generally found as about 60% up to 100% of the [Ser IL-8]$_{72}$/[Ala IL-8]$_{77}$ polypeptides.

Recombinant [Ala IL-8]$_{77}$ can be expressed in mammalian cells and purified as described for the natural endothelial [Ala IL-8]$_{77}$. Furthermore, recombinant [Ala IL-8]$_{77}$ can be obtained from transferred bacterial sources, for example E. coli. In this case, E. coli cells are transfected with a plasmid coding for a ubiquitin-methionyl-[Ala IL-8]$_{77}$ fusion protein, the fusion protein isolated and cleaved by CNBr treatment, and [Ala IL-8]$_{77}$ purified by ion exchange and reversed phase high performance liquid chromatography steps similar to those used to isolate natural [Ala IL-8]$_{77}$.

The subject polypeptides are characterized by having a molecular weight of 8 to 12 kilodaltons (kD), particularly about 10 kD as determined by gel electrophoresis. The sequence of [Ala IL-8]$_{77}$ is shown in FIG. 1.

Native endothelial-derived IL-8 has been identified as, at least, a mixture of [Ala IL-8]$_{77}$ and [Ser IL-8]$_{72}$. The present work provides purified [Ala IL-8]$_{77}$, substantially free of the [Ser IL-8]$_{72}$. It is recognized that modifications or derivatives of either of these molecule may be desirable to yield a therapeutically superior product. These derivatives, in particular, include alterations of the [Ala IL-8]$_{77}$ polypeptide by methods known in the art.

Desirable modifications may increase the potency with which the molecule inhibits leukocyte adhesion, increase its biological half life, serve to focus the activity at sites of inflammation, and/or eliminate or attenuate any undesirable side effects of the molecule.

[Ala IL-8]$_{77}$ Characteristics

Figure 2:
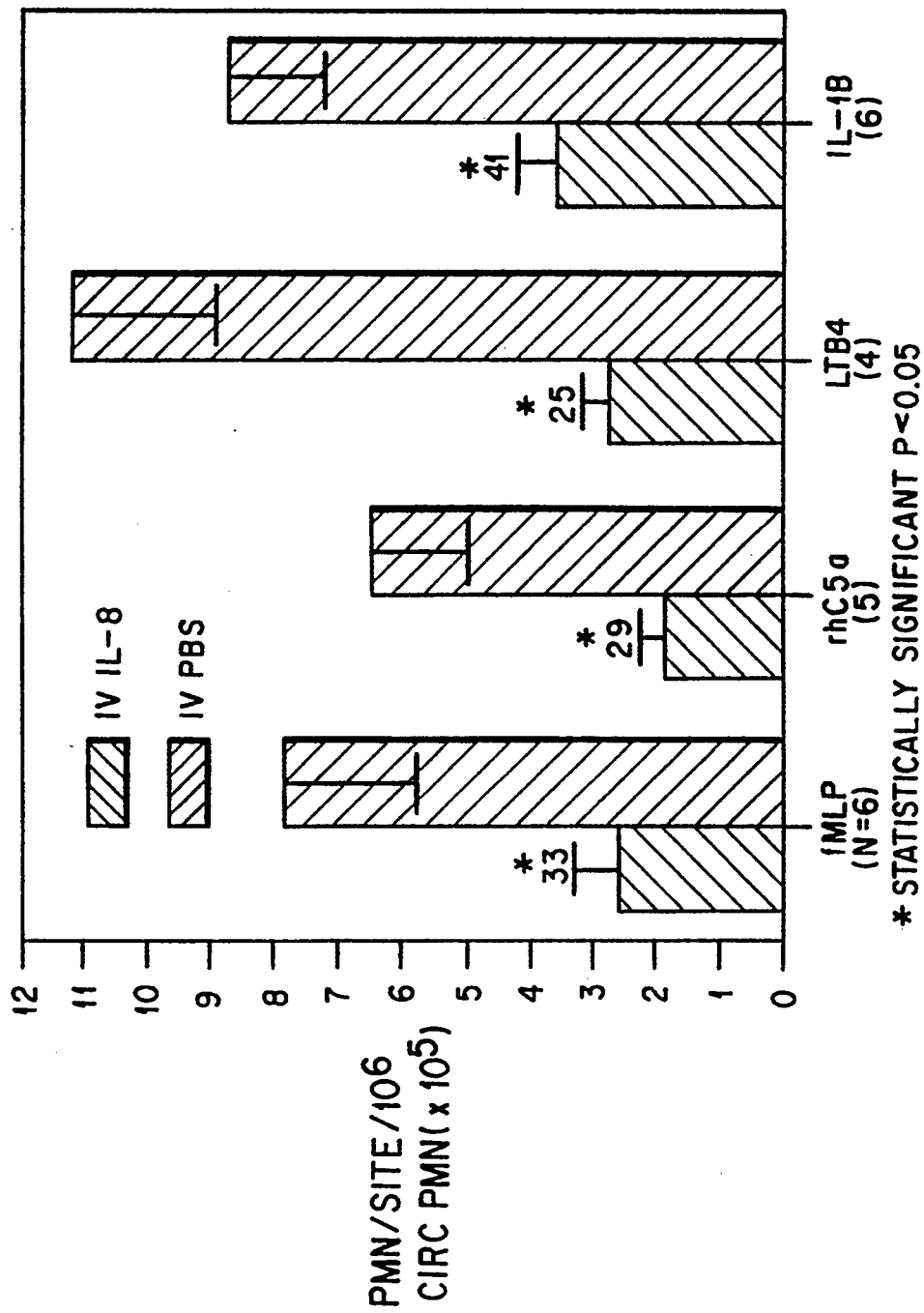
FIG. 2 Inhibition by [Ala IL-8]$_{77}$ of neutrophil infiltration into intradermal sites injected with inflammatory mediators. (See Example 10.)
Figure 3:
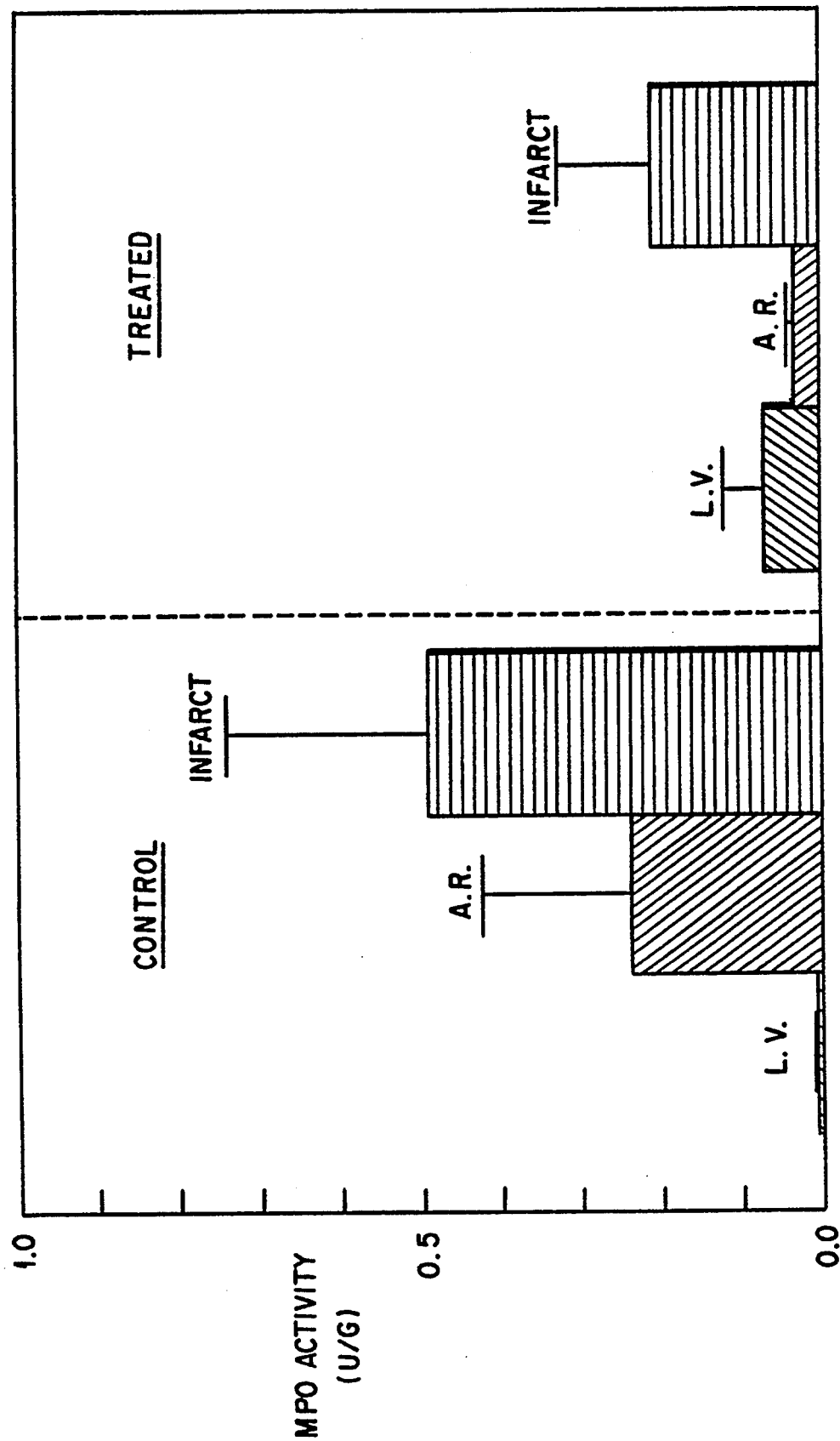
FIG. 3 Inhibition by [Ala IL-8]$_{77}$ of myeloperoxidase activity in a rabbit myocardial ischemia model. L.V.: left ventricle; A.R.: at risk, Infarct: infarcted area. The right and left panels present data from [Ala IL-8]$_{77}$-treated and control animals, respectively. (See Example 11.)

Our in vitro and in vivo studies indicate that [Ala IL-8]$_{77}$ finds use as an inhibitor of neutrophil extravasation and neutrophil-mediated tissue damage. Thus, [Ala IL-8]$_{77}$ administered to rabbits in an intravenous bolus, reduces neutrophil recruitment to intradermal sites injected with any of a variety of inflammatory mediators (FIG. 2). Furthermore, in a rabbit myocardial ischemia/reperfusion model an intravenously administered bolus of [Ala IL-8]$_{77}$ reduces infarct size and myeloperoxidase activity in the affected tissue (FIG. 3).

Figure 4A:
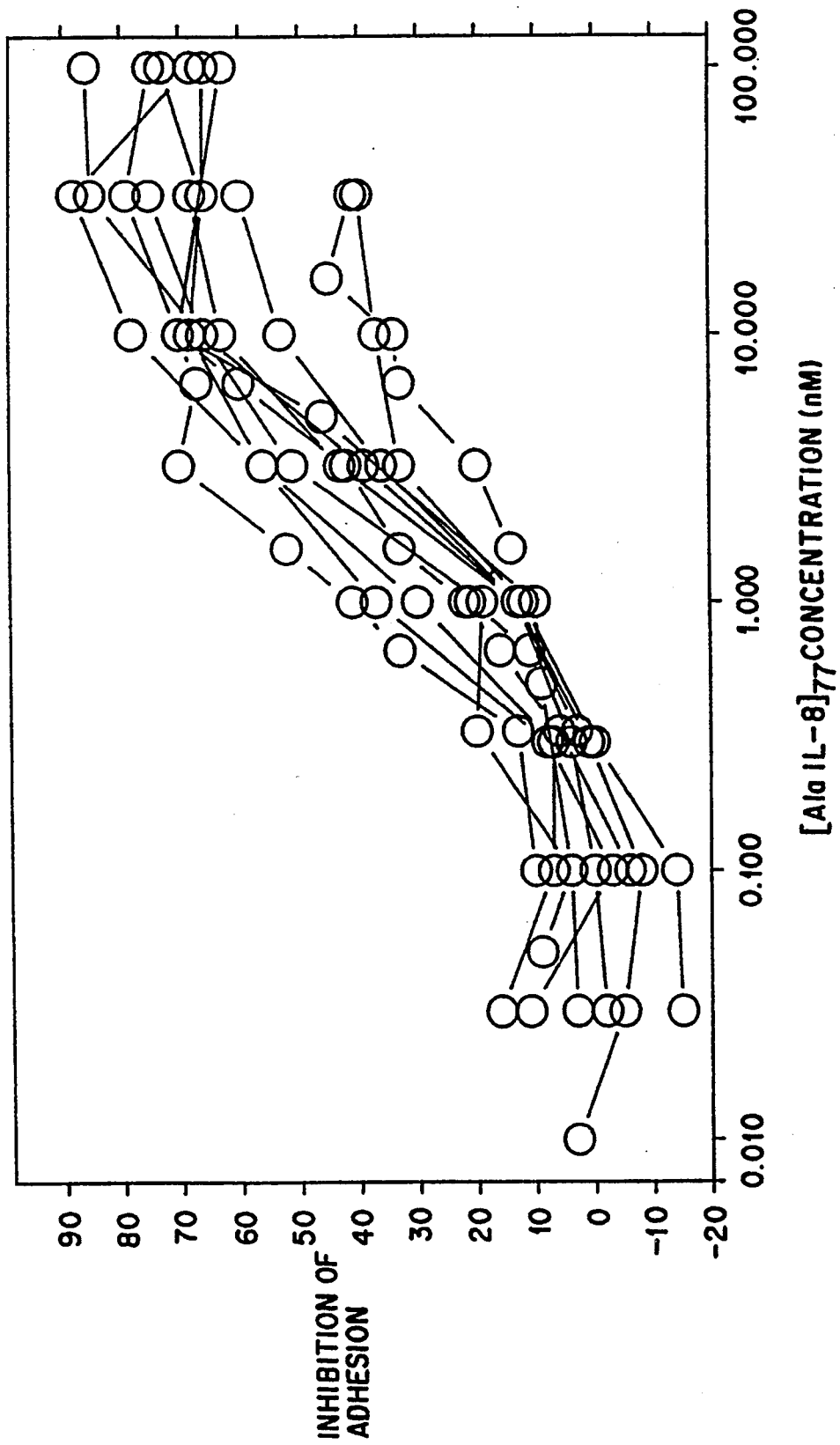
FIG. 4A–B Inhibition of neutrophil adhesion to IL-1-activated endothelium, mediated by [Ala IL-8]$_{77}$ (panel A) or IL-8 (panel B). Each panel shows multiple data sets. (See Example 13.)
Figure 4B:
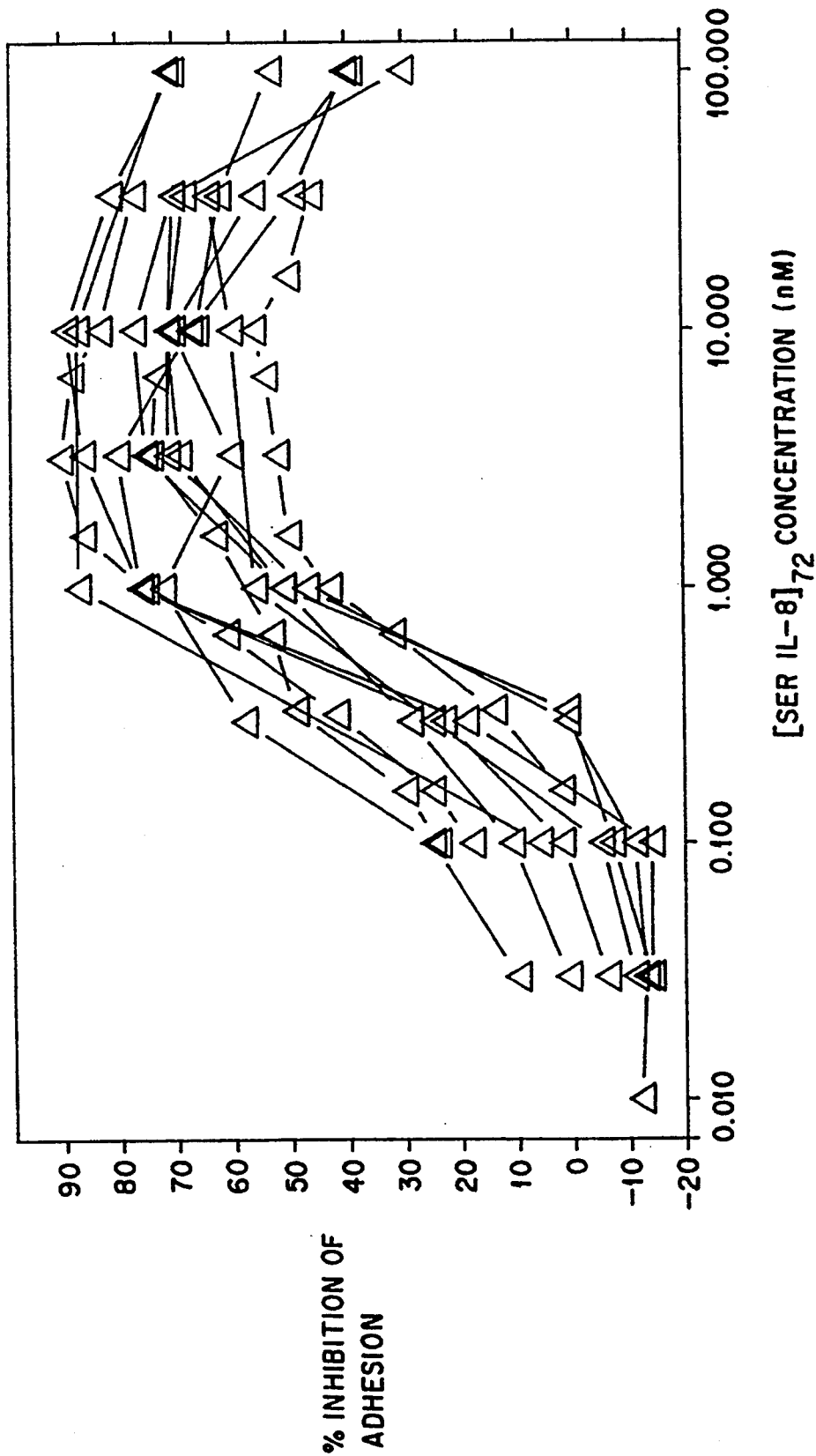

Our experiments show that [Ser IL-8]$_{72}$ has greater leukocyte adhesion inhibition activity in vitro than does [Ala IL-8]$_{77}$ (FIG. 4). However, the literature indicates that [Ser IL-8]$_{72}$ has potentially deleterious activities (causing neutrophil degranulation and superoxide production, Shroeder et al., *J. Immunol.* 139:3474 [1987]; Peveri et al., *J. Exp. Med.* 167:1547 [1988]) which may discourage systemic administration of IL-8. However, [Ala IL-8]$_{77}$ contains arginyl-seryl residues at positions 5 and 6. We have demonstrated (FIG. 5) that thrombin efficiently cleaves [Ala IL-8]$_{77}$ at this position to yield [Ser IL-8]$_{72}$. The literature indicates that inflamed endothelium develops procoagulant properties. Thus, contact of [Ala IL-8]$_{77}$ with inflamed endothelium can potentially generate a more potent LAI [Ser IL-8]$_{72}$ at the desired site of action (site of inflammation), while avoiding undesired side effects resulting from systemic exposure to [Ser IL-8]$_{72}$. Modified forms of [Ala IL-8]$_{77}$ may have increased capacity to be converted to more active forms at the site of inflammation.

Our data demonstrate that upon binding to the surface of the neutrophil, [Ala IL-8]$_{77}$ is converted to a lower molecular weight species, the electrophoretic mobility of which suggests that it is IL-8 (FIG. 6). The latter species, but not [Ala IL-8]$_{77}$ is internalized by the neutrophil (FIG. 6). This suggests that before cleavage, [Ala IL-8]$_{77}$ may lack certain activities, potentially deleterious, that result from signals transmitted by internalized [Ser IL-8]$_{72}$ ligand, and/or that [Ala IL-8]$_{77}$ may be resistent to neutrophil-mediated clearance until cleavage. In this regard, certain uncleavable mutant forms of [Ala IL-8]$_{77}$ may exhibit reduced undesired side effects, increased circulating half life, or both.

The present invention provides for substantially pure [Ala IL-8]$_{77}$. A substantially pure preparation is defined as containing predominantly [Ala IL-8]$_{77}$ polypeptides with less than 5% contaminating IL-8 polypeptides.

[Ala IL-8]$_{77}$ decreases adhesion of neutrophils to IL-1-activated endothelium detectably at less than about 0.3 nM, half maximally at about 1 to about 3 nM and maximally at about 5 to about 10 nM (FIG. 4). Moreover, [Ala IL-8]$_{77}$ and IL-8, at about 10 to about 50 nM, prevent neutrophil-mediated damage to cytokine activated endothelium (data not shown).

Figure 8:
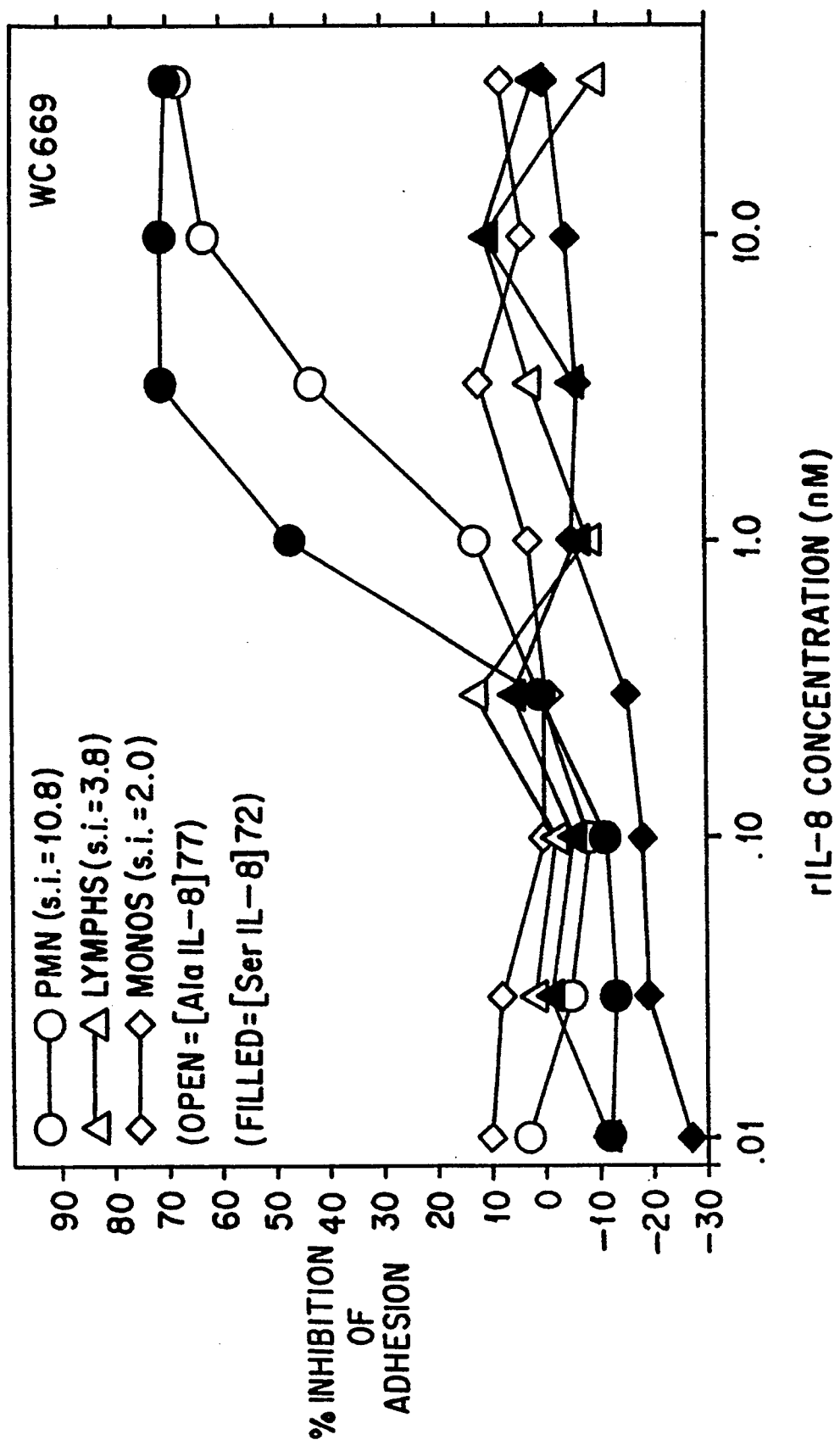
FIG. 8 [Ala IL-8]$_{77}$ inhibits the adhesion of neutrophils, but not of lymphocytes or monocytes, to IL-1-activated endothelium. (See Example 13.)

As indicated, the subject polypeptides find particular use as therapeutic agents. The polypeptides of the present invention offer advantages over other proposed anti-inflammatory drugs. Although [Ala IL-8]$_{77}$ and IL-8 inhibit neutrophil binding to activated endothelium they do not affect the binding of other leukocytes (e.g. monocytes, lymphocytes) to endothelium (FIG. 8). Thus, prolonged therapeutic administration of these polypeptides may not impair immune function. Further, while [Ala IL-8]$_{77}$ markedly reduces the adhesion of neutrophils to cytokine-activated or inflamed endothelium, it does not significantly affect the low basal level of adhesion of neutrophils to unactivated endothelium (data not shown). That is, activated endothelium is specifically targeted while there is no evidence that the normal interaction of neutrophils with endothelium is disturbed.

Figure 9:
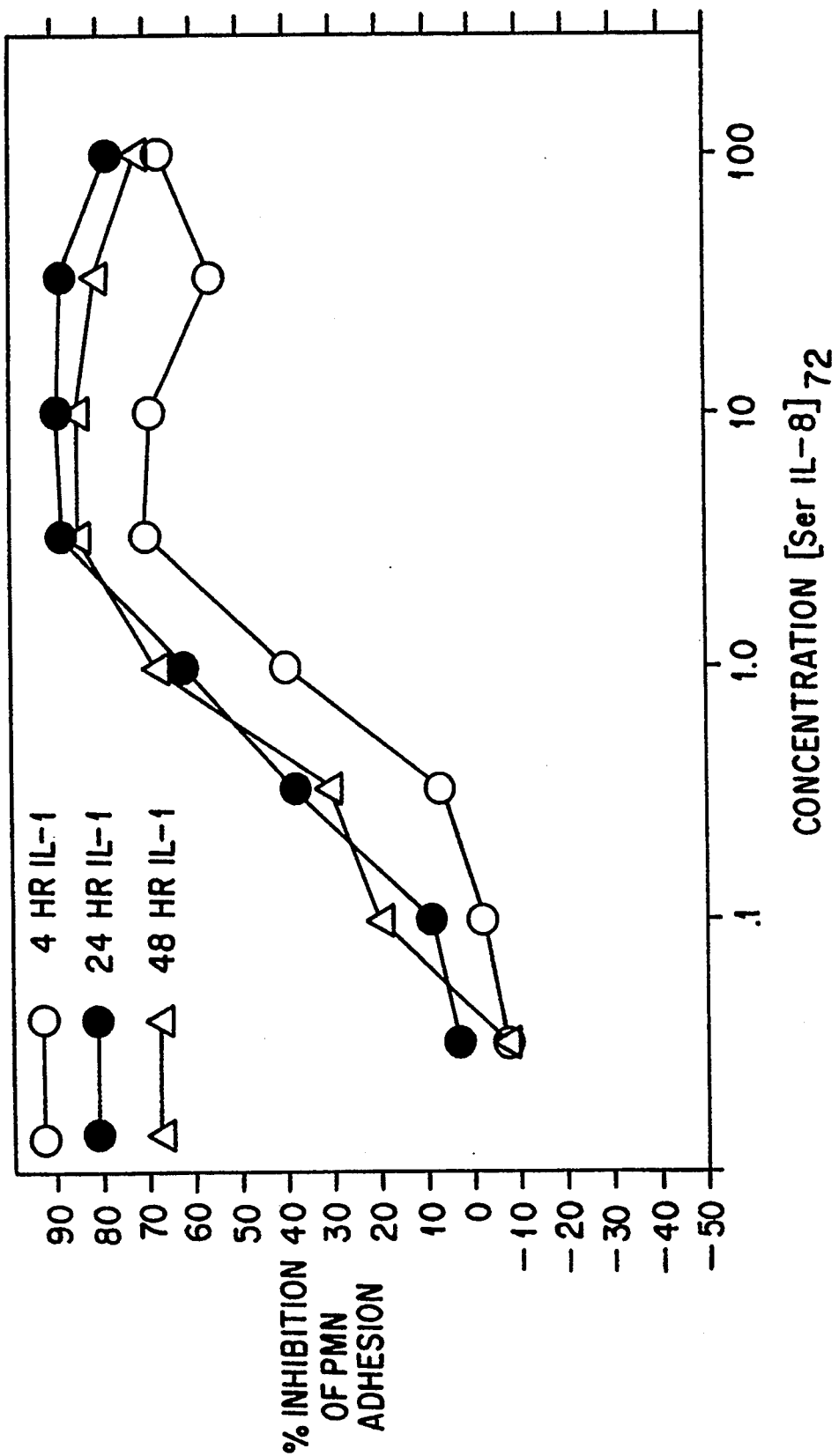
FIG. 9 [Ala IL-8]$_{77}$ inhibits the adhesion of neutrophils to HEC that have been stimulated with Il-1 for 4, 24 or 48 hr. (See Example 13.)

The leukocyte adhesion-inhibiting action of [Ala IL-8]$_{77}$ or IL-8 is not dependent on the expression of a particular adhesion receptor (see Example 13 and FIG. 9). This is in direct contrast with various anti-adhesion receptor monoclonal antibodies that have been proposed as potential anti-inflammatory drugs. Thus, IL-8 polypeptides are more efficient inhibitors, because different types of endothelial cell receptors mediate neutrophil adhesion over a span of time, e.g., as acute inflammation progresses to a chronic phase.

The polypeptides of the present invention may be useful in the treatment of adult respiratory distress syndrome, septic shock, vasculitis, ischemia-reperfusion injury in the heart and other vital organs, and other inflammatory disease processes in which leukocyte (neutrophil) dependent injury to vascular-endothelium or other tissues occurs. They may find particular use in the treatment of heart attacks, specifically to protect heart muscle from neutrophil-mediated damage after a heart attack.

Uses of [Ser IL-8]$_{72}$

As indicated above [Ser IL-8]$_{72}$ has previously been identified as promoting inflammation. Specifically, a monocyte-derived neutrophil chemotactic factor (MDNCF) has been reported as a potential mediator of leukocyte-specific inflammatory response, since it is released by an inflammatory stimulus and has the selective capacity to attract neutrophils but not monocytes. (See Yoshimura et al. *Proc. Nat'l. Acad. Sci. USA* 84:9233–9237 (1987). The amino acid sequence reported for this factor is essentially the same as [Ser IL-8]$_{72}$. However, no leukocyte adhesion inhibiting activity has been attributed to the purified molecule. Thus the present invention encompasses the use of purified or recombinant [Ser IL-8]$_{72}$, or derivatives thereof, as anti-inflammatory agents and as therapeutics for clinical indications in which leukocyte mediated damage of vascular endothelium or other tissues occurs.

As indicated [Ser IL-8]$_{72}$ has greater leukocyte adhesion inhibition activity in vitro than does (Ala-IL-8]$_{77}$. In fact, a comparison of the relative activities indicates that [Ser IL-8]$_{72}$ is about 10-fold more active than [Ala IL-8]$_{77}$, in inhibiting neutrophil adhesion to activated endothelium. Therefore, [Ser IL-8]$_{72}$ may be utilized where potent leukocyte adhesion inhibitors are needed, for example at specific sites of inflammation or, at sites of organ or tissue transplant.

Copending Applications, Serial No. 07/232,224, filed Aug. 15, 1988 and Ser. No. 07/442,786, filed Nov. 29, 1989, disclose an endothelial-derived leukocyte adhesion inhibitor (LAI), designated in the later filed application as endothelial-derived IL-8. Endothelial-derived IL-8 comprises a mixture of [Ala IL-8]$_{77}$ and [Ser IL-8]$_{72}$ polypeptides. The isolation of substantially pure components was not possible until the present work.

While preparations of natural endothelial-derived IL-8 inhibit both monocytes and neutrophil adhesion to cytokine-activated endothelial cultures, recombinant human [Ala IL-8]$_{77}$ and [Ser IL-8]$_{72}$ molecules do not inhibit monocyte or lymphocyte adhesion. This suggests a highly selective activity for the recombinant molecules limited to neutrophil adhesion. Therefore, recombinant polypeptides of the present invention are indicated as highly selective therapeutics. That is, they find particular use in neutrophil-dependent inflammatory processes and/or neutrophil-mediated tissue damage.

It is recognized that the methods for modifications, mutation, production and administration of [Ser IL-8]$_{77}$ polypeptides, discussed below, are applicable to [Ser IL-8]$_{72}$.

Both [Ser IL-8]$_{72}$ and [Ala IL-8]$_{77}$ polypeptides provide protection from neutrophil-mediated damage. It is noted that this protective action may not simply be a manifestation of inhibition of adhesion per se. Therefore, the present invention is not bound by any particular mechanism.

DNA Characterization

Several methods are available for the isolation of the nucleotide sequences of the subject polypeptides. As the amino acid sequence is known, DNA probes can be constructed from the amino acid sequence to be used for screening a genomic library to isolate the corresponding DNA sequence. The same DNA probes may also be used to screen a blood lymphocyte cDNA library, particularly a phorbol ester induced human peripheral blood lymphocyte cDNA library as demonstrated below in the Experimental Section. Alternatively, DNA fragments may be inserted into appropriate expression vectors and leukocyte adhesion and inhibition activity assayed. Further, the DNA sequence of FIG. 1 may be used to create probes for detecting the presence of genes or cDNA encoding [Ala IL-8]$_{77}$. The probe may contain about 12–100 continuous nucleotides from FIG. 1. More preferably, the probe may contain 14–50 nucleotides and most preferably 16–40 nucleotides.

DNA sequence analysis using the method of Messing et al. (Nuc. Acids Res. (1981) 9:309) has revealed the nucleotide sequence coding for IL-8 polypeptides (FIG. 1).

It is recognized that the nucleotide sequence may be altered by deletion, addition or mutation. Therefore, derivatives of the DNA sequence are encompassed by the present invention as long as the sequences code for a polypeptide with leukocyte adhesion-inhibiting activity of [Ala IL-8]$_{77}$.

Protein Modification

1. [Ala IL-8]$_{77}$ is the polypeptide originally derived from human endothelial cells having the amino acid sequence of FIG. 1, together with analogues and variants thereof having the biological activity of the corresponding native [Ala IL-8]$_{77}$. This term includes any analogue or variant thereof having an N-terminal extended form of [Ser IL-8]$_{72}$ or variants thereof, which inhibits leukocyte adhesion to endothelial cells or protects endothelial cells from neutrophil-mediated injury.

More specifically, analogues or variants of [Ala IL-8]$_{77}$ are defined as molecules in which the amino acid sequence or other feature of native [Ala IL-8]$_{77}$ has been modified covalently or noncovalently. Thus, variants may or may not have a molecular weight of approximately 10 kD (as determined by SDS-PAGE carried out in the absence of a reducing agent such as, e.g., $\beta$-mercaptoethanol or dithiothreitol). Amino acid sequence variants include not only allelic relatives of the FIG. 1 sequence, but also predetermined mutations thereof. Generally, amino acid sequence variants have an amino acid sequence with at least about 80% homology, and more typically at least about 90% homology, to that of the native [Ala IL-8]$_{77}$ of FIG. 1. Henceforth, the term [Ala IL-8]$_{77}$ shall mean either the native sequence or a variant form unless otherwise appropriate.

Thus, included within the scope of the present invention is an [Ala IL-8]$_{77}$ having the human [Ala IL-8]$_{77}$ amino acid sequence as set forth in FIG. 1, analogous [Ala IL-8]$_{77}$ proteins from other species such as bovine, equine, porcine, ovine, canine, murine, feline [Ala IL-8]$_{77}$, and the like, and biologically active amino acid sequence variants of these [Ala IL-8]$_{77}$ molecules, including alleles and in vitro-generated covalent derivatives of [Ala IL-8]$_{77}$ proteins that demonstrate its biological activity.

Modifications of [Ala IL-8]$_{77}$. Derivatives and amino acid sequence variants of [Ala IL-8]$_{77}$ are useful for their biological activity as it relates to therapeutic utility, as is set forth elsewhere herein, as well as for their ability to bind to anti-[Ala IL-8]$_{77}$ antibodies. The derivatives and variants possessing the latter characteristic are useful in purifying antibodies or, when labeled, as reagents in immunoassays for [Ala IL-8]$_{77}$, whether or not such derivatives and variants retain their therapeutic biological activity. Antibodies specific for [Ala IL-8]$_{77}$ but without affinity for [Ser IL-8]$_{72}$ may be conveniently used to distinguish and/or separate these related polypeptides.

The [Ala IL-8]$_{77}$ may be labeled with a detectible marker by any of the methods known to those in the biochemical sciences. Among the anticipated detectible markers are radioisotopes, enzymes, fluorophores, stable free radicals and metal ions.

a. Covalent modification

Covalent modifications of a [Ala IL-8]$_{77}$ molecule are included within the scope of this invention. Variant [Ala IL-8]$_{77}$ fragments having up to about 77 residues may be conveniently prepared by in vitro synthesis. Such modifications may be introduced into the molecule by reacting targeted amino acid residues of the purified or crude protein with an organic derivatizing agent that is capable of reacting with selected side chains or terminal residues. The resulting covalent derivatives are useful in programs directed at identifying residues important for biological activity.

Cysteinyl residues most commonly are reacted with $\alpha$-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, $\alpha$-bromo-$\beta$-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'-N-C-N-R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking the [Ala IL-8]$_{77}$ to a water-insoluble support matrix or surface for use in the method for purifying anti[Ala IL-8]$_{77}$ antibodies. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W. H. Freeman & Co., San Francisco, pp. 79–86 [1983]), acetylation of the N-terminal amine, and, in some instances, amidation of the C-terminal carboxyl group.

b. Mutation(s) in the DNA

Amino acid sequence variants of [Ala IL-8]$_{77}$ can also be prepared by mutations in the DNA as shown in FIG. 1. Such variants include, for example, deletions from, or insertions or substitutions of, residues within the amino acid sequence shown in FIG. 1. Any combination of deletion, insertion, and substitution may also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure (see EP 75,444A).

At the genetic level, these variants ordinarily are prepared by site-directed mutagenesis of nucleotides in the DNA encoding the [Ala IL-8]$_{77}$, thereby producing DNA encoding the variant, and thereafter expressing the DNA in recombinant cell culture. The variants typically exhibit the same qualitative biological activity as the naturally occurring analog.

While the site for introducing an amino acid sequence variation is predetermined, the mutation per se need not be predetermined. For example, to optimize the performance of a mutation at a given site, random mutagenesis may be conducted at the target codon or region and the expressed [Ala IL-8]$_{77}$ variants screened for the optimal combination of desired activity. Techniques for making substitution mutations at predetermined sites in DNA having a known sequence are well known, for example, site-specific mutagenesis.

Preparation of [Ala IL-8]$_{77}$ variants in accordance herewith is preferably achieved by site-specific mutagenesis of DNA that encodes an earlier prepared variant or a nonvariant version of the protein. Site-specific mutagenesis allows the production of [Ala IL-8]$_{77}$ variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., *DNA*, 2:183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira et al., *Meth. Enzymol.*, 153:3 [1987]) may be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., Proc. Natl. Acad. Sci. (USA), 75:5765 (1978). This primer is then annealed with the single-stranded protein-sequence-containing vector, and subjected to DNA-polymerizing enzymes such as E. coli polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected that include recombinant vectors bearing the mutated sequence arrangement.

After such a clone is selected, the mutated protein region may be removed and placed in an appropriate vector for protein production, generally an expression vector of the type that may be employed for transformation of an appropriate host.

c. Types of Mutations

Amino acid sequence deletions generally range from about 1 to 30 residues, more preferably 1 to 10 residues, and typically are contiguous. Mutations of [Ala IL-8]$_{77}$ may be in the N-terminal or in the [Ser IL-8]$_{72}$ portion of the polypeptide.

Amino acid sequence insertions include amino- and/or carboxyl-terminal fusions of from one residue to polypeptides of essentially unrestricted length, as well as intrasequence insertions of single or multiple amino acid residues. Intrasequence insertions (i.e., insertions within the mature [Ala IL-8]$_{77}$ sequence) may range generally from about 1 to 10 residues, more preferably 1 to 5, most preferably 1 to 3. An example of a terminal insertion includes fusion of a heterologous N-terminal signal sequence to the N-terminus of the [Ala IL-8]$_{77}$ molecule to facilitate the secretion of mature [Ala IL-8]$_{77}$ from recombinant hosts.

The third group of variants are those in which at least one amino acid residue in the [Ala IL-8]$_{77}$ molecule, and preferably only one, has been removed and a different residue inserted in its place. An example is the replacement of arginine 5 and/or serine 6 by other amino acids to render the [Ala IL-8]$_{77}$ resistent to proteolysis by thrombin, thereby creating a more stable [Ala IL-8]$_{77}$ analogue. When arginine 5 of [Ala IL-8]$_{77}$ is replaced by another amino acid not susceptible to cleavage by thrombin, or other proteases, the resulting polypeptide is suitable as an antagonist to [Ser IL-8]$_{72}$. Any amino acid may be substituted for arginine 5. However, those without a positive charge on the amino acid side chain are preferred. Such substitutions preferably are made in accordance with the following Table 1 when it is desired to modulate finely the characteristics of a [Ala IL-8]$_{77}$ molecule.

TABLE 1

| Original Residue Substitutions | Exemplary |
| --- | --- |
| Ala (A) | gly; ser |
| Arg (R) | lys |
| Asn (N) | gln; his |
| Asp (D) | glu |
| Cys (C) | ser |
| Gln (Q) | asn |

TABLE 1-continued

| Original Residue Substitutions | Exemplary |
| --- | --- |
| Glu (E) | asp |
| Gly (G) | ala; pro |
| His (H) | asn; gln |
| Ile (I) | leu; val |
| Leu (L) | ile; val |
| Lys (K) | arg; gln; glu |
| Met (M) | leu; tyr; ile |
| Phe (F) | met; leu; tyr |
| Ser (S) | thr |
| Thr (T) | ser |
| Trp (W) | tyr |
| Tyr (Y) | trp; phe |
| Val (V) | ile; leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to produce the greatest changes in [Ala IL-8]$_{77}$ properties will be those in which (a) glycine and/or proline (P) is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Most deletions and insertions, and substitutions in particular, are not expected to produce radical changes in the characteristics of the [Ala IL-8]$_{77}$ molecule. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native [Ala IL-8]$_{77}$-encoding nucleic acid, expression of the variant nucleic acid in recombinant cell culture, and, optionally, purification from the cell culture, for example, by bioassay of the variant's activity or by immunoaffinity adsorption on a rabbit polyclonal anti-[Ala IL-8]$_{77}$ column (to absorb the variant by binding it to at least one remaining immune epitope).

Since [Ala IL-8]$_{77}$ may aggregate into dimers (Clore et al., J. Biol. Chem. 264:18907 [1989]), it is within the scope hereof to provide hetero- and homodimers, wherein one or both subunits are variants. Where both subunits are variants, the changes in amino acid sequence can be the same or different for each subunit chain. Heterodimers are readily produced by cotransforming host cells with DNA encoding both subunits and, if necessary, purifying the desired heterodimer, or by separately synthesizing the subunits, dissociating the subunits (e.g., by treatment with a chaotropic agent such as urea, guanidine hydrochloride, or the like), mixing the dissociated subunits, and then reassociating the subunits by dialyzing away the chaotropic agent.

The activity of the cell lysate or purified [Ala IL-8]$_{77}$ variant is then screened in a suitable screening assay for the desired characteristic. For example, a change in the immunological character of the [Ala IL-8]$_{77}$ molecule, such as affinity for a given antibody, is measured by a competitive-type immunoassay. Changes in the enhancement or suppression of anti- or pro-inflammatory activities by the candidate mutants are measured by the appropriate assay. Modifications of such protein properties as redox or thermal stability, hydrophobicity, susceptibility to proteolytic degradation, or the tendency to aggregate with carriers or into multimers are assayed by methods well known to the ordinarily-skilled artisan.

3. [Ala IL-8]$_{77}$ Expression and Formulation

The polypeptides can be produced recombinantly by insertion of corresponding DNA into an appropriate expression vector, for example, pBR322 or its derivative pRK5. The plasmid pRK5 is discussed in detail in European Patent Publication No. 0307247. The resulting plasmids are used to transfect a cell culture, either prokaryotic or eukaryotic. An example of a eukaryotic cell is human 293 cells. An example of a prokaryotic cell for expression is *Escherchia coli*. Methods for transfection include the calcium precipitation method or other available methods known in the art.

The preferred method of isolating natural or recombinant [Ala IL-8]$_{77}$ utilizes cation ion exchange chromatography using resins such as carboxymethyl cellulose or Sepharose, fast flow S-Sepharose or Mono S (Pharmacia). The chromatography of [Ala IL-8]$_{77}$, or of the [Ser IL-8]$_{72}$ is conducted at pH greater than 8, and more preferably at pH greater than 8.5.

A preferred method for producing [Ala IL-8]$_{77}$ or [Ala IL-8]$_{72}$ utilizes an amino terminal fusion protein wherein ubiquitin is fused at the amino terminus with a methionine at the junction. DNA encoding this fusion protein is used in recombinant expression systems. The separation of the ubiquitin is accomplished using cyanogen bromide.

It is recognized that the subject compounds can be used in a variety of ways, both in vivo or in vitro. Antibodies can be prepared in conventional ways, as in the method described in U. S. Pat. No. 4,574,116 and the references cited therein.

The subject polypeptides can be formulated into pharmaceutical compositions according to known methods of preparing pharmaceutically useful compositions. In this manner, the polypeptides are combined in a mixture with a pharmaceutically acceptable carrier vehicle. Suitable vehicles and their formulation, including other human proteins, e.g., human serum albumin, are described, for example, in *Remington's Pharmaceutical Sciences* (16th ed., Osol, A., ed., Mack, Easton, Pa. [1980]). In order to form a pharmaceutically acceptable composition suitable for effective administration, such compositions will contain a therapeutically effective amount of the subject polypeptides (an inflammation-reducing amount or a leukocyte adhesion-inhibiting amount), together with a suitable amount of carrier vehicle. The leukocyte adhesion-inhibiting and inflammation-reducing amounts can be determined by in vivo pharmacologic studies, as well as in vitro cell adhesion assays.

The polypeptides may be formulated as a sterile pharmaceutical composition for therapeutic use which is suitable for intravenous administration. The product may be in lyophilized form to be reconstituted for use by the addition of a suitable carrier, or diluent, or alternatively, it may be in the form of an aqueous solution.

For reconstitution of a lyophilized product in accordance with the present invention, one may employ a sterile diluent, which may contain materials generally recognized for approximating physiological conditions. In this manner, the sterile diluent may contain a buffering agent to contain a physiologically acceptable pH, such as sodium chloride, saline, phosphate-buffered saline, and/or other substances which are physiologically acceptable and/or safe for use.

When used as an aqueous solution, the pharmaceutical composition, for the most part, will contain many of the same .substances described above for the reconstitution of a lyophilized product.

The polypeptides useful in the methods of the present invention may be employed in such forms as, for example, sterile suspensions for injection or encapsulated for targeting to specific tissue sites with antibodies directed to inflammation-related cell surface structures. See, for example, Bevilacqua et al., *PNAS USA* 84:9238–9242 (1987); Cotran et al., *J. Exp. Med.* 164:661–666 (1986). The polypeptides may also be injected directly into an inflamed site, such as an inflamed joint, a specific site of inflammation, or directly into the area surrounding tissue transplants.

The [Ala IL-8]$_{77}$ may be used in combination with (1) anti-inflammatory compounds such as aspirin, acetominophen, ibuprofen or glucocorticoids;

(2) immuno suppressive compounds such as tumor necrosis factor, transforming growth factor-$\beta$, interferon $\alpha$, interferon-$\beta$, interferon-$\gamma$, or antibodies directed to surface receptors found in the immune system cells such as the ICAM or ELAM or their ligands;

(3) thrombolytic compounds such as tissue plasminogen activator, urokinase or eminase; or (4) anti-thrombotic compounds such as heparin and argatroban.

Where the subject polypeptides are to be administered to a host as an anti-inflammatory agent, the polypeptides may be administered, for example, topically, intraarterially, intraperitoneally, intravenously, intrapleurally, intraoccularly, by injection, subcutaneously, or the like. Administration by injection includes continuous infusion as well as single or multiple boluses.

The amount of the subject polypeptide administered will vary with the manner of administration, the concurrent use of other active compounds, host size, type and spread of inflammation, and the like. Generally, the polypeptide will be administered in sufficient doses to obtain an effective concentration of about 1 nM to about 10 nM, usually about 5 nM of the polypeptide in the blood. The dosage amount of polypeptides necessary to obtain the desired concentration in the blood can be determined by pharmacokinetic studies.

Additional pharmaceutical methods may be employed to control the duration of action. Controlled release preparations may be achieved through the use of polymers to complex or absorb the subject polypeptides. The controlled delivery may be achieved by selecting appropriate macromolecules (for example, polyesters, polyamino acids, polyvinyl, polypyrrolidone, ethylenevinylacetate, methylcellulose, carboxymethylcellulose, or protamine sulfate) the appropriate concentration of macromolecules, as well as the methods of incorporation. In this manner release of the polypeptides can be controlled.

Another possible method useful in controlling the duration of action by controlled release preparations is the incorporation of the subject polypeptides into particles of a polymeric material such as polyesters, polyamino acids, hydrogels, poly(lactic acid), or ethylenevinylacetate copolymers.

Alternatively, instead of incorporating the subject polypeptides into polymeric particles, it is possible to entrap these materials in microcapsules prepared, for example, by coacervation techniques or by interfacial polymerization, for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules) or in macroemulsions. Such techniques are disclosed in Remington's Pharmaceutical Sciences (1980).

The following examples are offered by way of illustration and not by way of limitation.

EXAMPLES

EXAMPLE 1

Purification of Natural Endothelial LAI (mixture of [Ala IL-8]$_{77}$ and IL-8). LAI activity was produced by incubating (37 C., 8 h) confluent monolayers (second and third passage) of human umbilical vein endothelial cells (Wheeler, M. E. et al., J. Clin. Invest. 822:1211 (1988); Luscinskas, F. W. et al., J. Immunol. 142:2257 (1989)) with recombinant human rh IL-1$\beta$ (5–10 U/ml) in serum-free RPMI 1640 containing insulin, transferrin and selenium (ITS, 1 ml/l, Collaborative Research, Cambridge, Mass.). Conditioned medium was sterilely collected on wet ice, clarified by centrifugation, and stored at −70 C. Upon thawing, 0.2 to 0.5 liter aliquots were adjusted to pH 3.0 with trifluoracetic acid (TFA) and, at 4 C., sequentially ultrafiltered through 30 kD and 5 kD YM membranes (Amicon Inc., Danvers, Mass.). The concentrated (50×) YM-5 retentate was spin-dialyzed against TFA in Milli-Q water (pH 3.0), lyophilized, dissolved in anion exchange column equilibration buffer (10 mM Tris.Cl, 6M urea, 0.01% Tween 80, pH 8.0), and separated on a Mono Q HR 5/5 column. [Ala IL-8]$_{77}$ activity, recovered in the unbound material, was concentrated by Centricon 10 ultrafiltration (Amicon), diluted with cation exchange buffer (25 mM sodium acetate, 6M urea, 0.01% Tween 80, pH 5.0), and separated on a Mono S HR 5/5 column. Bound proteins were eluted using a three-stage linear gradient of NaCl in equilibration buffer (0.15M NaCl in 5 min, 0.5M NaCl in 40 min, 1M NaCl in 50 min; flow rate, 0.5 ml/min). Column fractions (2 ml) were prepared for bioassay by spin dialysis against RPMI with bovine albumin (0.4 mg/ml, Cohn Fraction V). Twenty-four hour conditioned medium was treated similarly, except that YM-30 filtration and lyophilization were omitted and 0.15M NaCl was added to the Mono S equilibration buffer. Activity was quantified using a modified endothelial-leukocyte adhesion assay (Bevilacqua, M. P., et. al., J. Clin. Invest. 76:2003 (1985); Bevilacqua, M. P., et al., Proc. Natl. Acad. Sci. USA 84:9238 (1987); Bevilacqua, M. P., Science 243:1160 (1989).

Figure 10A:
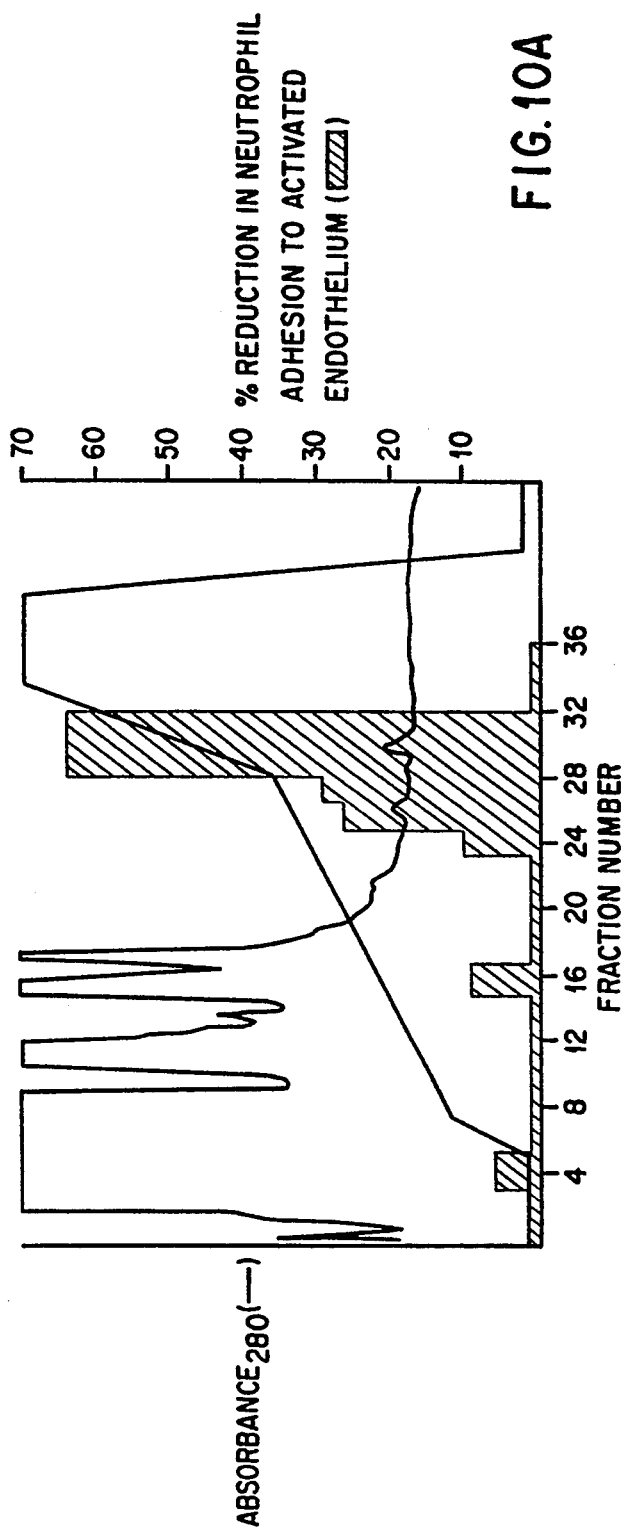
FIG. 10A–C (A) Purification of leukocyte adhesion inhibitor (LAI) activity from medium conditioned by IL-1 activated HEC. Pooled fractions from a Mono S column (5) were assayed (6) in triplicate at 1:8 final dilution. The dashed line indicates NaCl concentration gradient. One of three representative experiments. (B) Concentration-dependent effect (mean±SD, n=3) of pooled fractions 28–31 on neutrophil adhesion to IL-1 activated HEC. One of two representative experiments. (C) Silver-stained SDS gel (7) of pooled fractions 28–31. (See Example 1.)
Figure 10B:
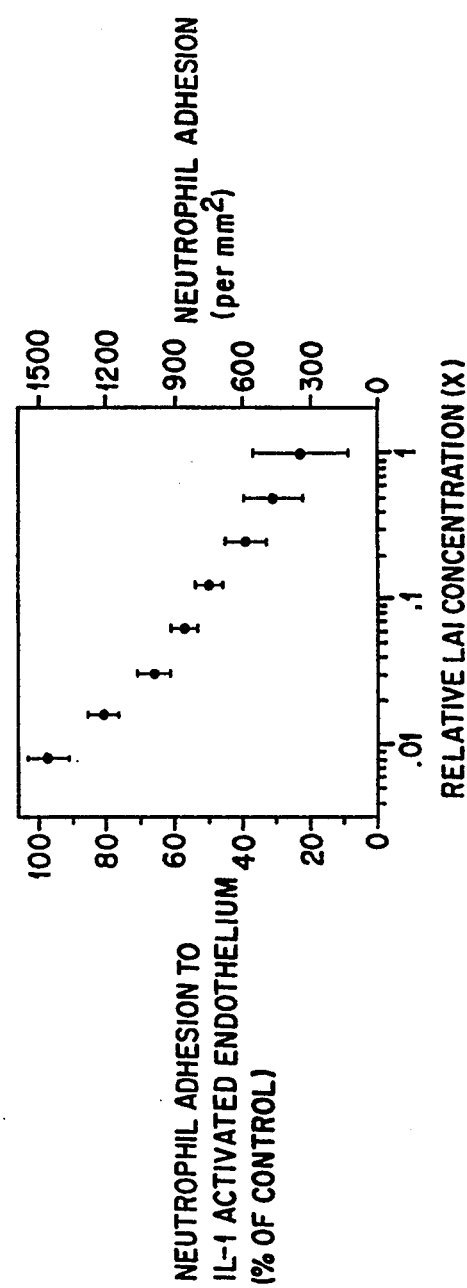
Figure 10C:
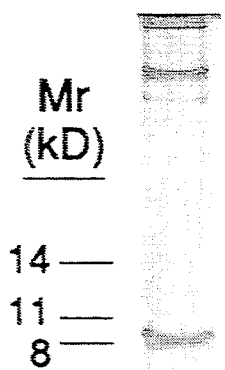

The leukocyte adhesion-inhibitory activity secreted by IL-1 -treated HEC activity cofractionated with a small protein peak that eluted from the Mono S cation exchange column at high ionic strength (FIG. 10A). The pool of maximally active fractions (28–31) inhibited neutrophil adhesion to IL-1 activated HEC in a concentration-dependent fashion (FIG. 10B). When analyzed by gel electrophoresis (FIG. 10C; nonreduced samples in 12% acrylamide gels, performed as described by Schagger and von Jagow, Anal. Biochem. 166:368 [1987]) this partially purified material contained a prominent 10-kD protein.

Pooled peak fractions were subjected to 53 cycles of NH$_2$-terminal sequencing by a modification of the method of Edman and Begg, Eur. J. Biochem. 1:80 (1967), using 0.1M Quadrol (pH 10.0), phenylisothiocyanate (Beckman Instruments) and TFA (Applied Biosystems) as reagents. Samples were applied in solution to a reversed-phase sequencing column and washed with water before sequencing. The reversed-phase cartridge was then loaded onto a prototype gas-liquid phase sequencer (EP-257735). The 2-anilino-5-thiazoiinone from each cycle was converted to the phenylthiohydantoin derivatives for identification on a Hewlett Packard 1090 L liquid chromatograph. The predominant (>90%) sequence was: NH$_2$-AVLPRSAKELRC-QCIKTYSKPFHPKFIKELRVIESGPHCAN-TEIIVKLSDGRE. This does not represent the complete amino acid sequence of the protein. Mass spectrometry indicated that the complete protein was identical to [Ala IL-8]$_{77}$ (data not shown). [Single letter abbreviations for the amino acid residues are: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.]

This is almost identical to the sequence of interleukin-8 (IL-8) (Yoshimura, T., et al., Proc. Natl. Acad. Sci. USA 84:9233 [1987]; Lindley, I., et al., Proc. Natl. Acad. Sci. USA 85:9199 [1988]; Van Damme, J., et al., J. Exp. Med. 167:1364 [1988]; Gregory, H. et al., Biochem. Biophys. Res. Comm. 151:883 [1988]), the 72 amino acid neutrophil-activating polypeptide that is secreted by activated T cells and monocytes. The term "interleukin-8 (IL-8)," (Larsen, C. G., et al., Science 243:1464 [1989]) designates the polypeptide produced by stimulated human peripheral blood lymphocytes and monocytes, that has been referred to variously as neutrophil activating peptide-1 (NAP-1) (Larsen, C. G. et al., above), neutrophil chemotactic factor (NCF) (Yoshimura, T., et al., J. Immunol. 139:788 [1987]), monocyte-derived neutrophil chemotactic factor (MDNCF) (Yoshimura, T. et al., Proc. Natl. Acad. Sci. usa 84:9233 [1987]), neutrophil-activating factor (NAF) (Peveri, P., et al., J. Exp. Med. 167:1547 [1988]; Lindley, I., et al., Proc. Natl. Acad. Sci. USA 85:9199 [1988]), and monocyte-derived and lymphocyte-derived neutrophil-activating peptide (MONAP/LYNAP) (Shroeder, J. M., et al., J. Immunol. 139:3474 [1987]). However, the predominant endothelial-derived polypeptide, here designated [Ala IL-8]$_{77}$, differed from the predominant [70–100% (Yoshimura, T., et al., Proc. Natl. Acad. Sci. USA 84:9233 [1987]; Lindley, I., et al., Proc. Natl. Acad. Sci. USA 85:9199 [1988]; Van Damme, J., et al., J. Exp. Med. 85:9199 [1988]; Van Damme, J., et al., J. Exp. Med. 167:1364 [1988]; Gregory, H. et al., Biochem. Biophys. Res. Comm. 151:883 [1988]) form of mononuclear leukocyte-derived IL-8, by having a pentapeptide AVLPR extension at the NH$_2$-terminus. The endothelial cell-derived material contained IL-8 as a minor component (7% in 8 hour conditioned medium, 20% in 24 hour conditioned medium; three preparations each).

Final purification of endothelial LAI/IL-8 was by reversed-phase HPLC on an Aquapore (C-8) RP-300 guard column equilibrated with 0.1% TFA in water. A linear 0 to 60% gradient of acetonitrile containing 0.1%

TFA was developed (flow rate, 0.5 ml/min). Endothelial LAI/IL-8 forms eluted in approximately 35% acetonitrile. The purified 10 kD protein was lyophilized prior to bioassay, $NH_2$-terminal sequencing, and quantitative amino acid analysis.

The resulting 10-kD protein potently inhibited the amplified (20 to 62 times) neutrophil adhesion observed with IL-1 activated HEC, with an $EC_{50}$ of 0.5 to 1.0 nM (threshold, <0.3 nM; range of maximum inhibition, 3 to 30 nM). Reduced inhibitory activity was noted at high (>50 nM) concentrations. In contrast to the marked inhibition (up to 80%) observed with cytokine-activated HEC monolayers, the adhesion of unstimulated neutrophils to unactivated monolayers ("basal adhesion", 61±26 neutrophils per $mm^2$, mean±SD, four experiments) was not significantly reduced by the purified protein, and at very high concentrations was increased (100 nM, 2.5 fold; 500 nM, 5 fold).

EXAMPLE 2

Expression of Recombinant [Ala IL-8]$_{77}$ in *Mammalian Cells*. Complementary DNA for [Ala IL-8]$_{77}$/IL-8 was isolated from a phorbol ester induced human peripheral blood lymphocyte cDNA library (Gray et al., *Nature* 312:721 [1984]) by screen with a synthetic DNA oligonucleotide probe based on the $NH_2$-terminal amino acid sequence of IL-8. An 800 bp HpaII-NheI fragment spanning the entire coding region of IL-8 was inserted into the mammalian expression vector pRK5 between the ClaI and the XbaI sites and the multiple cloning region downstream from the cytomegalovirus promoter. The resulting plasmid, pRK.hg.8k, was used to transfect human 293 cells by the $CaPO_4$/DNA precipitation method (10 micrograms of plasmid DNA/100 mm culture dish). Conditioned medium was harvested after 72 hours and centrifuged to remove cell debris prior to chromatography on S-Sepharose.

EXAMPLE 3

Separation of [Ala IL-8]$_{77}$ and IL-8. Human 293 cells transfected with an IL-8-containing plasmid secreted both [Ala IL-8]$_{77}$ and IL-8. As indicated by the following procedures, the relative abundance of the two variants secreted into the medium was 80% and 20%, respectively. The two forms could be resolved by SDS-PAGE using a 16% acrylamide Tris/Tricine-buffered gel system. The identity of the upper and lower protein bands as [Ala IL-8]$_{77}$ and IL-8, respectively, was established by N-terminal sequencing of material electroblotted onto an Immobilon membrane. An additional arginine residue in the long form confers a slight pI difference between the two variants (pI=9.54 for [Ala IL-8]$_{77}$ vs. 9.34 for IL-8). It was reasoned that this might allow their resolution by cation exchange chromatography at basic pH.

Seventy-two hour conditioned medium from 293 cells transfected with pRK5-IL-8 was clarified by centrifugation and brought to 25 mM sodium acetate, 6M urea, 0.01% Tween 80, pH 5.0. The medium was loaded onto a 2 ml S-Sepharose column equilibrated with 25 mM sodium acetate, 0.15M NaCl, 6M urea, 0.01% Tween 80, pH 5.0. Bound proteins were eluted with 100 ml of a linear 0.15M to 1M NaCl gradient. Electrophoresis of nonreduced samples in 16% acrylamide gels was carried out in a Tris/Tricine system (Schagger and von Jagow, *Anal. Biochem.* 166:368 [1987]). Column fractions (3 ml) containing IL-8 species were pooled. Centricon 10 ultrafiltration units (Amicon) were used to concentrate the protein and replace the buffer with cation exchange equilibration buffer (10 mM Tris. Cl, 4M urea, 0.01% Tween 80, pH 8.7). The sample was loaded onto a Mono S HR 5/5 column and bound proteins were eluted with a linear gradient of 0.5M NaCl in equilibration buffer (to 0.14M NaCl in 10 min) followed by an isocratic elution at 0.14M NaCl for 40 min (0.5 ml/min). Fractions containing [Ala IL-8]$_{77}$ (0.5 ml) were pooled and prepared for bioassay using a Centricon 10 ultrafiltration unit (Amicon) for protein concentration and buffer exchange into PBS +0.04% RIA-BSA. Column fractions (0.5 ml) enriched in [Ala IL-8]$_{77}$ were subjected to reiteration of the Mono S step while fractions enriched in the IL-8 were converted to pure IL-8 by thrombin cleavage as described in Example 4.

FIG. 7 shows the separation of [Ala IL-8]$_{77}$ and IL-8 that was achieved. Contamination of [Ala IL-8]$_{77}$ with IL-8 was less than 2% as indicated by N-terminal sequencing and mass spectrometry. This chromatography step thus constitutes a simple and effective method to purify [Ala IL-8]$_{77}$ away from contaminating IL-8.

EXAMPLE 4

Figure 5:
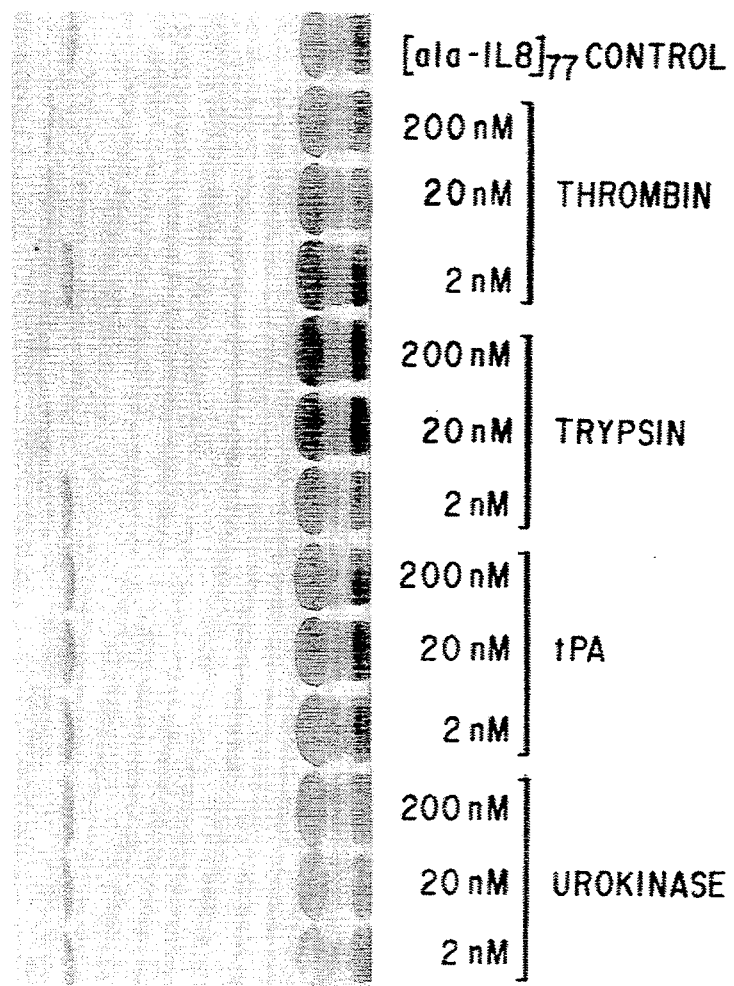
FIG. 5 Conversions of [Ala IL-8]$_{77}$ to IL-8 by thrombin and trypsin, but not by tPA or urokinase. Note the increase in [Ala IL-8]$_{77}$ electrophoretic mobility following thrombin or trypsin treatment. Incubations with proteases were for 30 min at 37 C. (See Example 4.)

Proteolytic conversion of [Ala IL-8]$_{77}$ to IL-8. The [Ala IL-8]$_{77}$ polypeptide contains an arginine-serine sequence at positions 5 and 6 which represents a potential cleavage site for arg-specific proteases. Therefore, we incubated purified [Ala IL-8]$_{77}$ with either trypsin, thrombin, urokinase, or tissue-type plasminogen activator (tPA) for 30 minutes at 37 C. Treatment with thrombin converted [Ala IL-8]$_{77}$ to a form that comigrated with IL-8 on SDS gels (FIG. 5). N-terminal sequencing confirmed that the lower molecular weight form was in fact IL-8. Like thrombin, trypsin also converted [Ala IL-8]$_{77}$ to a form that comigrated with IL-8. In contrast, urokinase and tPA, even at 200 nM doses, caused no detectable cleavage of [Ala IL-8]$_{77}$ (FIG. 5). We found no evidence that thrombin cleaved [Ala IL-8]$_{77}$ at any other sites than between arg5 and ser6, even when the concentration of the protease was increased to 200 nM. However, trypsin at 200 nM converted [Ala IL-8]$_{77}$ to multiple cleavage products.

To isolate IL-8 from a preparation containing [Ala IL-8]$_{77}$ a Mono S Centricon 10 ultrafiltration unit (Amicon) was used to concentrate the Mono S fractions enriched in IL-8 and exchange the buffer into PBS containing 1 mM $CaCl_2$. The resulting sample was incubated at 37° C. for 1 hour in the presence of 200 nM thrombin (Calbiochem), diluted 1:4 in cation exchange equilibration buffer and subjected to the Mono S chromatographic steps described in Example 3. The IL-8 fractions (0.5 ml) were pooled, and prepared for bioassay for concentration in Centricon 10 ultrafiltration units (Amicon) and buffer exchange into PBS+0.04% RIA-BSA. The IL-8 concentration was determined after buffer-exchange using a competitive RIA.

This strategy can thus be used to convert a mixture of the two IL-8 forms into pure IL-8.

EXAMPLE 5

Bacterial Expression of [Ala IL-8]$_{77}$. Biologically active recombinant [Ala IL-8]$_{77}$ was produced in *E. coli* by expression of a ubiquitin-methionyl-[Ala IL-8]$_{77}$ fusion protein, followed by purification of the fusion protein, release of [Ala IL-8]$_{77}$ by CNBr cleavage and subsequent purification of [Ala IL-8]$_{77}$.

It is noteworthy that *E. coli* express ubiquitin-[Ala IL-8]$_{77}$ fusion protein in large quantity, whereas *E. coli* express [Ala IL-8]$_{77}$ poorly. This expression method has application in expression of [Ala IL-8]$_{77}$ in a variety of bacterial cell types.

Construction of Plasmid Which Expresses Ubiquitin [Ala IL-8]$_{77}$ Fusion Protein. DNA encoding ubiquitin [Ala IL-8]$_{77}$ fusion protein was constructed by inserting a synthetic DNA fragment deduced from amino acid sequences expected at the junction between ubiquitin and [Ala IL-8]$_{77}$ (RGGMAVLPRSAKELRCQCIK-TYSKPFHPKFIKELRVIESGPHCANTEIIVKL). Synthesis of oligonucleotide was carried out as described (Froehler, B. C., Ng, P. G., and Matteucci, M. D. (1986) Nucleic Acid Res. 14, 5399-5407, Froehler, B. C. and Matteucci, M. D. (1986) Tetrahedron Letters 27, 469-472). Six oligonucleotides ranging from 50 to 60 residues (30 ng each) were phosphorylated and ligated together in a single reaction mixture containing 50 mM Tris-HCl (pH 8.0), 10 mM MgCl, 0.5 mM ATP, 10 units of T4 polynucleotide kinase, and 1000 units of T4 DNA ligase. The resultant DNA duplex was digested with Sac II and HindIII and fractionated in a 6% polyacrylamide gel. The DNA corresponding to the 150 base pair fragment was excised and electroeluted. The eluted DNA was extracted with chloroform, precipitated with ethanol and ligated to a SacII and HindIII cleaved ubiquitin fusion protein expression plasmid similar to that described previously (Miller, H. I., Henzel, W. J., Ridgway, J. B., Kuang, W. J., Chisholm, V., and Liu, C. C. (1989) Bio/technology, 7, 698-704, Liu, C. C., Miller, H. I., Kohr, W. J. and Silber, J. I. (1989) J. Biol. chem. in press). The remaining coding region of [Ala IL-8]$_{77}$ protein was completed by inserting the 586 base pair HindIII-HindIII fragment (from plasmid pRK 3-10C) into the HindIII cleaved DNA derived from the plasmid constructed above. The DNA sequences encoding the fusion protein were verified by dideoxynucleotide DNA sequencing analysis. The expression of the fusion protein is under the control of the promoter derived from the *E. coli* trp operon and can be induced by the addition indoleacrylic acid (Kleid, D., Yansura, D., Small, B., Dowbenko, D., Moore, D. M., Grubman, M. J., McKercher, P. D., Morgan, D. O., Robertson, B. H. & Bachrach, H. L. (1981) Science 214, 1125-1129).

EXAMPLE 6

Purification of Recombinant [Ala IL-8]$_{77}$ from *E. coli*. To purify the fusion protein from *E. coli* transfected with the above plasmid, sedimented and washed *E. coli* paste was resuspended in 2 l of lysis buffer (25 mM sodium acetate, 50 mM NaCl, 25 mM EDTA, 1.0 mM PMSF, pH 5.7). The cells were broken in a microfluidizer at 45 psi and the lysate buffer was adjusted to contain 6M urea, 0.01% Tween 80. The mixture was applied to a Fast Flow S-Sepharose column equilibrated with the above adjusted lysate buffer. After washing the column with this buffer and then with this buffer adjusted to 0.2M NaCl, bound proteins were eluted using a 2 l linear NaCl gradient (NaCl concentration increasing from 0.2M to 0.5M). Peak fractions containing the prominent 18 KDa protein were made 1 mM in fresh PMSF and concentrated by ultrafiltration with a "20 k MWCO" Sartorius membrane unit. (Recovery at this stage was estimated to be >90%). The concentrated, partially purified fusion protein was dialyzed against 50 mM TrisCl (pH 8.0) at 5° C., clarified by centrifugation at 3000 g for 5 min., and concentrated in Amicon 10 KDa MW cutoff Centriprep units. This material was stored at −70° C. until CNBr cleavage.

Fusion protein (20 mg/1 ml) was cleaved by incubation in the dark for 12 hours in 70% formic acid using a one hundred fold molar excess of CNBr per methionine residue. The reaction solution was lyophilized, resuspended in Mono S equilibration buffer (10 mM TrisCl, 6M urea, 0.01% Tween 80, 50 mM NaCl, pH 8.7), and loaded onto a Mono S column. The [Ala IL-8]$_{77}$ polypeptide was eluted using a multistage gradient (NaCl concentrations increasing from 50 mM to 0.4M).

Figure 11:
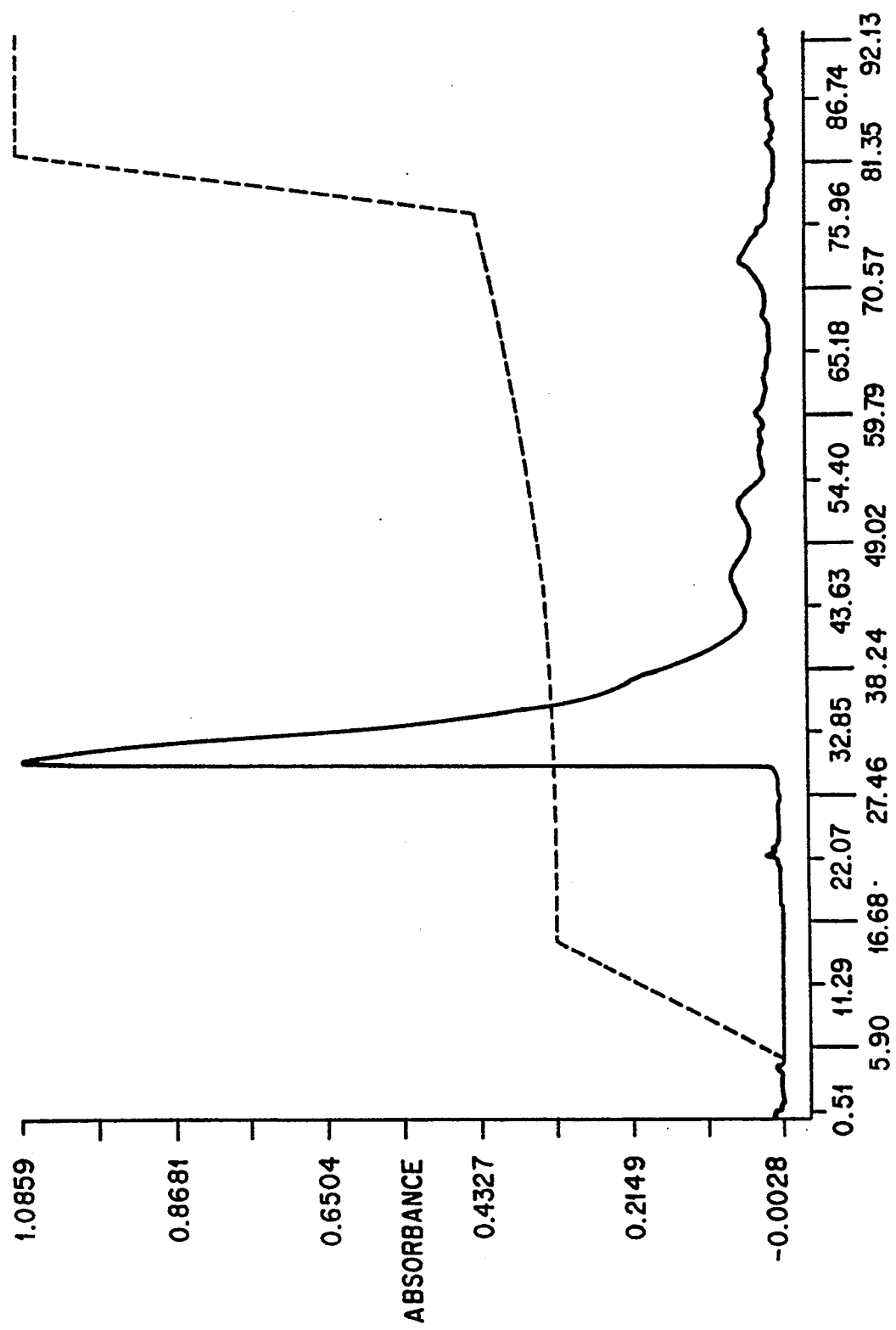
FIG. 11 Optical density 280 nM profile of E. coli-expressed [Ala IL-8]$_{77}$ eluting from a Brownlee RPC-8 reversed phase HPLC column. Final purification step: the concave CH$_3$CN gradient profile is shown. Y-Axis: O.D. at 280 nM; X-Axis: minutes. (See Example 5.)

Fractions containing [Ala IL-8]$_{77}$ were detected using Tris/Tricine gels as described above, concentrated using Centricon 10 filters, and injected onto a Brownlee RPC-8 reverse phase HPLC column equilibrated with 0.1% TFA. The column was eluted by developing a concave gradient using 0.1% TFA in acetonitrile. FIG. 11 shows the optical density profile (280 nM absorption) of [Ala IL-8]$_{77}$ eluting from this column. The fractions containing the pure [Ala IL-8]$_{77}$ were pooled, lyophilized, redissolved in H$_2$O, relyophilized, and stored at −70° C.

SDS-PAGE with silver staining analysis, HPLC optical density at 280 nM, and mass spectrometry all indicated that this material was >95% pure. This protocol yielded preparations free of endotoxin, as determined by the limulus amoebocyte lysis assay (Levin and Bang, *Thromb. Diath. Haemorrh.* 19:186 [1968]). IL-8 could be generated from this recombinant [Ala IL-8]$_{77}$ by thrombin treatment, essentially as described above for recombinant [Ala IL-8]$_{77}$ expressed in mammalian cells.

Figure 12A:
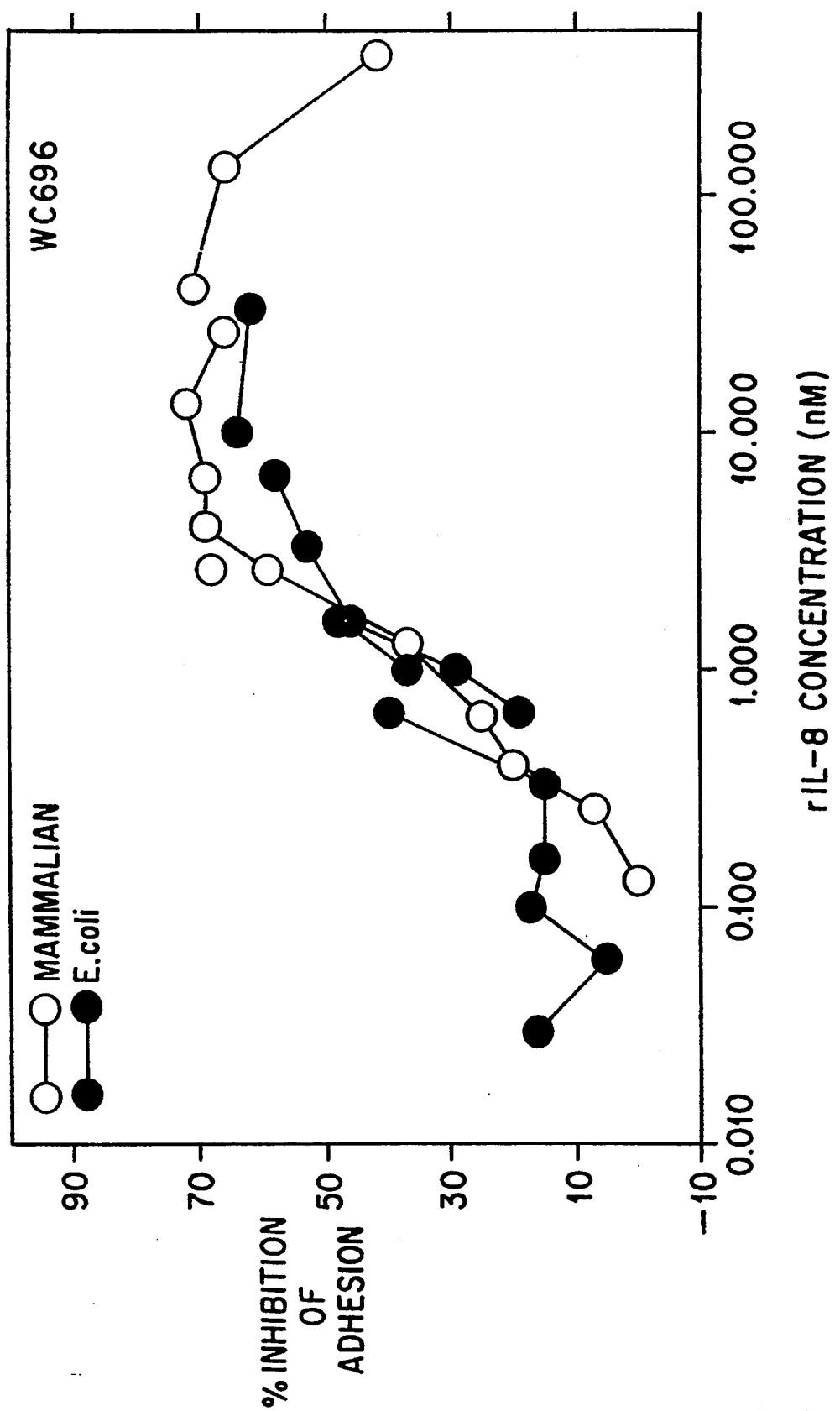
FIG. 12A–B Relative LAI activities of [Ala IL-8]$_{77}$ (panel A) and IL-8 (panel B) expressed in E. coli (closed symbols) and mammalian 293 cells (open symbols). (See Example 5.)
Figure 12B:
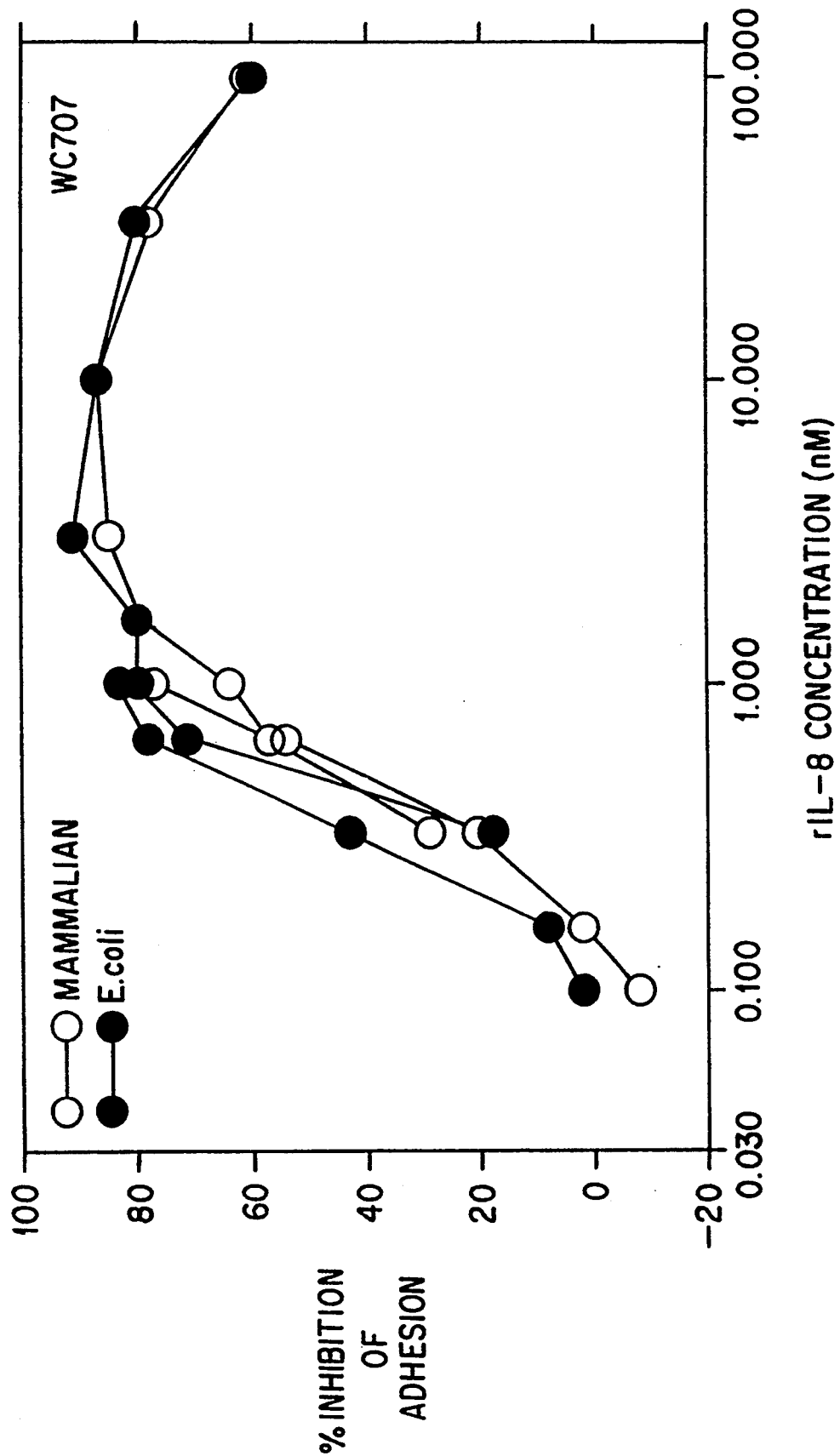

Recombinant [Ala IL-8]$_{77}$ and IL-8 obtained from *E. coli* exhibited LAI activities that were similar to those of [Ala IL-8]$_{77}$ and IL-8 expressed by mammalian cells (FIG. 12).

EXAMPLE 7

Radioimmunoassay (RIA). A New Zealand white rabbit was injected s.c. on the back with 100 μg of ubiquitin-IL-8 fusion protein (UQ-IL-8) in Freund's Complete Adjuvant and boosted with 100 μg UQ-IL-8 in Freund's Incomplete Adjuvant at 3 week intervals. To obtain serum the animal was bled from the ear vessels. Antibody titers were tested in an indirect ELISA utilizing mammalian recombinant IL-8 absorbed to plastic and alkaline phosphatase-coupled goat anti-rabbit IgG.

Test antigen or IL-8 standards were incubated with rabbit anti-IL-8 antiserum 12-18 hr. at 5° C. in RIA buffer (PBS/0.5% BSA/0.05% Tween 20/1M NaCl/0.02% NAN$_3$). Tracer $^{125}$I-IL-8 ($2 \times 10^4$ cpm) was added and the mixtures incubated at room temperature for 3 hours. Goat anti-rabbit IgG antiserum (1:10) in RIA buffer was incubated with the mixtures for 1 hour at room temperature and immune complexes were precipitated by addition of 6% PEG 8000 to final 4% concentration, and centrifugation (20 min., $2 \times 10^3$ g at 5° C.). Supernatants were decanted and pellets counted in a gamma counter.

EXAMPLE 8

Leukocyte Adhesion Inhibition Assay. The ability of [Ala IL-8]$_{77}$ and IL-8 to inhibit leukocyte adhesion to IL-1 stimulated endothelial cells was tested as previously described. Briefly, confluent human umbilical vein endothelial cell monolayers in 96 well microtiter plates (Costar Corp., Cambridge, Mass.) were preincubated with or without 5 U/ml rhIL-1beta. After 4 hours, the culture medium was aspirated, the monolayers washed and IL-8 or control samples were added to replicate wells. Human polymorphonuclear leukocytes (97% neutrophils) labeled with the fluorescein derivative BCECF (Molecular probes, Eugene, Oreg.) were then added to the microtiter wells (final concentration, $2 \times 10^5$ neutrophils/well, final volume, 0.1 ml). After 10 min at 37° C., the plates were sealed, inverted and centrifuged (250×G, 5 min), and the supernatants removed. The number of adherent neutrophils was calculated from the monolayer-bound fluorescence read in an automatic microtiter plate fluorimeter.

EXAMPLE 9

Endothelial Protection Assay. Human endothelial cells were grown to confluency on gelatin-coated microtiter wells as previously reported (Wheeler et al., *J. Clin. Invest.* 82:1211 [1988]). The monolayers were then washed twice with medium (RPMI+1% FBS). One hundred μl of medium ±10 units/ml rhIL-1β was added to each well and incubated 4 hrs. at 37° C. After the IL-1 treatment the monolayers were washed once with medium. Human blood PMN were then added ($2 \times 10^5$ to $2 \times 10^6$/well) in 100 μl medium containing test material (for rhIL-8, 1 to 500 nM were tested). The plates were then incubated at 37° C. for time periods ranging from 10 minutes to 2 hrs. After this incubation period, wells were filled with medium, sealed, inverted, and spun at 250 g for 5 minutes. The wells were then drained of fluid and fixed by adding 100 μl 2% paraformaldehyde for 15 minutes. Following fixation, wells were stained with Wright's-Geimsa stain and examined microscopically to determine the amount of PMN adherence and extent of damage to the endothelial monolayers.

EXAMPLE 10

Rabbit Intradermal Leukocyte Accumulation Model

A. Leukocyte Preparation. Rabbit neutrophil preparation and labelling were performed by a modified technique described by Issekutz and Movat (Issekutz, A. C. and Movat, H. Z. *Lab. Invest.* 42:310, 1980). In brief, leukocyte rich plasma (LRP) was prepared from citrate dextrose anticoagulated rabbit blood by hydroxyethyl cellulose sedimentation. Neutrophils were then isolated to >90% purity from the LRP by Percoll density gradient centrifugation. The neutrophil leukocytes were radioactively labelled with $^{51}$chromium, washed to remove any unbound radioactivity, and then resedimented in hydroxyethyl cellulose to dilute any $^{51}$chromium-labelled erythrocyte contaminant (Cybulsky M. I., Cybulsky I. J. and Movat H. Z. *Am. J. Path.* 124:1, 1986).

B. Quantitation of Neutrophil Emigration in Intradermal Sites of Inflammation. The chromium-labelled neutrophils were aliquoted and transfused into New Zealand White rabbits. Blood samples were obtained from a different site during the course of the experiment for the determination of white blood cell (WBC) count, WBC differential (per cent neutrophil vs. mononuclear leukocyte), and neutrophil specific activity (radioactivity per neutrophil).

Recombinant human interleukin-8 [Ala IL-8]$_{77}$, *E. coli* expressed, was intravenously administered as a bolus 20 minutes after infusion of the chromium-labelled neutrophils, to obtain a calculated initial circulating concentration of approximately 15 nM. Each intravenous IL-8-treated rabbit was paired with a control rabbit which received only a saline injection. Inflammatory mediators were injected intradermally in quadruplicate into the dorsal skin of both rabbits 30 minutes after IL-8 or PBS bolus. This time interval was selected since it allowed for the recovery of a significant neutropenia which was observed to follow IL-8 bolus. The mediators included formyl-methionyl-leucyl-phenylalanine (FMLP), ($10^{-10}$ moles/site), recombinant human complement c5a ($10^{-10}$ moles/site), leukotriene B$_4$ ($10^{-10}$ moles/site), and recombinant human interleukin-1β ($10^-$ moles/site).

Two hours after intradermal injection the rabbits were sacrificed and the radioactivity in the intradermally injected sites was measured in a gamma-spectrophotometer (Issekutz, A. C. and Movat, H. Z. *Immunology Letters.* 1:27, 1979). The number of neutrophils accumulating over the 2-hour period was obtained by dividing the radioactivity in a site by the blood neutrophil specific activity.

FIG. 2 shows that *E. coli*-expressed recombinant [Ala IL-8]$_{77}$, administered to a rabbit in an intravenous bolus markedly depressed the accumulation of neutrophils into intradermal sites injected with either of the following proinflammatory agents: formyl-methionyl-leucyl-phenylalanine (FMLP), C5a, leukotriene B4, and IL-1β. The [Ala IL-8]$_{77}$ mediated inhibition ranged from 59%, in the case of IL-1β, to 75%, in the case of LTB4.

EXAMPLE 11

Rabbit Myocardial Ischemia/Reperfusion Model. Male New Zealand rabbits anaesthetized with 2.5 ml Hypnorm i.m. were used. The trachea was cannulated and the animals respired with 18-24 ml (tidal volume room air) at 25-34 breaths/min.

The right carotid artery was cannulated and a cannula fed into the left ventricle for ventricular pressure recording. The right common jugular vein was cannulated for the administration of drugs and supplemental pentobarbital anaesthesia. The left femoral artery was cannulated for peripheral blood pressure recording. A lead II ECG was used to monitor the electrical conductivity of the heart. A loose 3.0 prolene ligature was placed around the first antero-lateral branch of the left coronary artery (LAL) approx. 1 cm from its origin.

After completion of all surgical procedures the animals were left for 15-30 min. to stabilize. Following a ten min. control recording period the LAL was occluded and was maintained closed for 60 min. After 30 min. of ischaemia a bolus dose of [Ala IL-8]$_{77}$ (50 μg in 500 μl distilled water, flushed through with 5 ml saline) was given. After 60 min. of ischaemia the ligature was opened to allow reperfusion of the ischaemic area for the next 4 hours.

Throughout the experimental period (5 hrs. 10 min.) diastolic, systolic and mean arterial pressure, heart rate, pressure rate product, left ventricular pressure, +dp/dt, −dp/dt, and ECG parameters including ST segment elevation were continuously monitored and recorded every 10 min.

At the end of the experimental period the LAL was reoccluded and 10 ml on Evans Blue (1% in saline) was infused via the left ventricle and the animal euthanised with pentobarbital overdose. The heart was quickly excised, washed in saline and the left ventricle dissected clear of the atria, right ventricle, any fat deposits, the valves and the papillary muscles, and weighed. The unstained area was dissected out and designated "the area at risk". The "normal" left ventricle tissue was weighed and placed on dry ice. The area at risk was then weighed, cut into 2-3 mm slices and placed in p-nitroblue tetrazolium (0.5 mg/ml) and incubated at 37° C. for 15 min. The infarcted area (unstained) was then dissected out and weighed. The infarct tissue and the viable portion of the area at risk were then placed on dry ice and stored at −70° C. until measured for myeloperoxidase content.

Arterial blood samples (1.5 ml into EDTA 3ml draw tubes) were taken throughout the course of the experiment at the following time points.

TABLE 2

| Real Time (min.) | Real Time (hours) | Time in Relation to [Ala IL-8]$_{77}$ (min.) |
|---|---|---|
| 10 | | −30 |
| 25 | | −15 |
| 35 | | −5 |
| | [Ala IL-8]$_{77}$ bolus and begin infusion | |
| 70 | 1'10" | 30 |
| 130 | 2'10" | 120 |
| 200 | 3'20" | 160 |
| 230 | 3'50" | 190 |
| 250 | 4'10" | 210 |
| 310 | 5'10" | 270 |

Blood cells in these samples were counted and the remainder centrifuged (3000 rpm 15 min.) to separate the plasma.

The bolus injection of 50 μg [Ala IL-8]$_{77}$ in the rabbit had no effect on heart rate, blood pressure, pressure rate product,/dp/dt. However, the peptide may have reduced the development of an elevated ST segment elevation in the 3 animals studied. These preliminary experiments suggest that [Ala IL-8]$_{77}$ reduced infarct size in this model of occlusion and reperfusion from control levels of 72±8% to 57±5% of the area at risk, which remained constant at 34±7% and 38±6% of the left ventricle for the control and [Ala IL-8]$_{77}$-treated groups, respectively. Subsequent measurement of the myeloperoxidase activity in the tissues (FIG. 3) shows that [Ala IL-8]$_{77}$ reduced this activity in both the area at risk (by 86%) and in the infarcted tissue (by 57%). This is consistent with the 28% increase in the healthy tissue and with the observations that [Ala IL-8]$_{77}$ increases the number of neutrophils in the circulation.

EXAMPLE 12

$^{125}$I-IL-8 Binding Assays. Isolated neutrophils were incubated at 37 C. for the indicated times with 0.5 mM radioiodinated [Ala IL-8]$_{77}$ or IL-8 in the absence (total binding) or presence of a thousand-fold excess unlabeled [Ala IL-8]$_{77}$ or IL-8 (nonspecific binding), or various concentrations of unlabeled [Ala IL-8]$_{77}$ or IL-8 ranging from 0.1 to 320 ng/ml (competitive binding). The binding medium was Ca$_{2+}$ and Mg$_{2+}$-free Hanks-buffered saline with 25 mM Hepes and supplemented with 0.5 % BSA. At the end of the incubation period, the triplicate samples (10$^6$ cells/point in 200 μl) were overlaid on 500 μl sucrose cushions (20% sucrose, 0.1% BSA in PBS) and centrifuged at 13 Kg in a microfuge for 3 min. The supernatant was removed by aspiration and the neutrophil pellet counted in a gamma-counter. Internalized $^{125}$I-IL-8 ligand was defined as that which resisted extraction from neutrophils during 10 min incubation at 5 C. in 0.1M glycine-HCl, pH 3 (Bajpai and Baker, Biochem. Biophys. Res. Commun. 133:475 [1985]).

The initial experiments were carried out with $^{125}$I-[Ala IL-8]$_{77}$ or $^{125}$I-IL-8 at 0.5 nM, a concentration expected to be less than required to saturate IL-8 receptors, based on the above in vitro bioassay results. Binding of the radioiodinated ligands to neutrophils was found to be extremely rapid, reaching 50% of the steady state level of specific binding within 1 min (data not shown). Nonspecific binding was measured with nonlabeled Il-8 at 0.5 μM, a concentration anticipated to be, and later demonstrated to be (vide infra), many fold grater than the Kdiss.

Figure 6A:
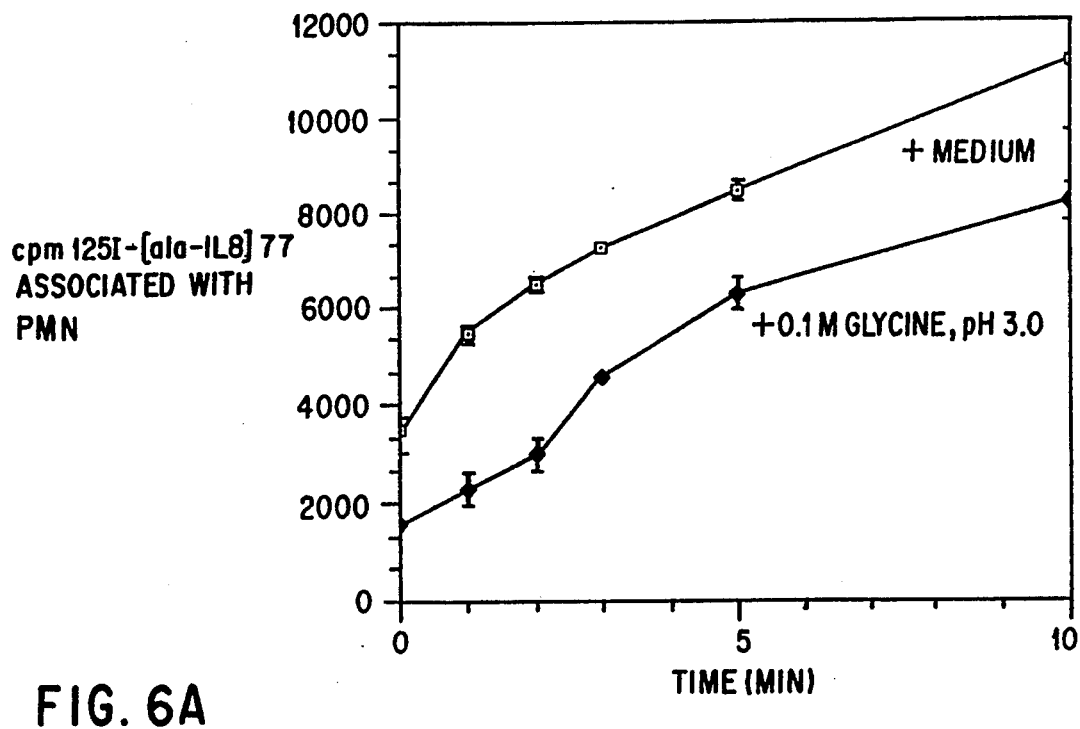
FIG. 6A–C Internalization of $^{125}$I-[Ala IL-8]$_{77}$ by neutrophils. $^{125}$I-[Ala IL-8]$_{77}$ (5 ng/ml) was incubated at 37 C. with human neutrophils (10$^6$ neutrophils/point) for various lengths of time. The PMN were then sedimented in a microfuge (2,000 rpm; 2 min) to remove to binding medium and incubated for 10 min at 4 C. in 0.1M Glycine HCl, pH 2.7 or in medium. The PMN were sedimented in a microfuge (13,000 RPM; 3 min) and the acid supernatant or medium were removed. SDS-PAGE sample buffer was immediately added to both acid supernatants and pellet samples. The radioactivity associated with the samples was measured with a gamma counter and the radiolabelled proteins were resolved by Tris/Tricine gel electrophoresis and autoradiography (C). The acid-stable and the total $^{125}$I-IL-8 bound to neutrophils were plotted as a function of incubation time (A). The acid-resistant IL-8 associated with the neutrophils was expressed as percent of total IL-8 bound to neutrophils and plotted as a function of incubation time (B).
Figure 6B:
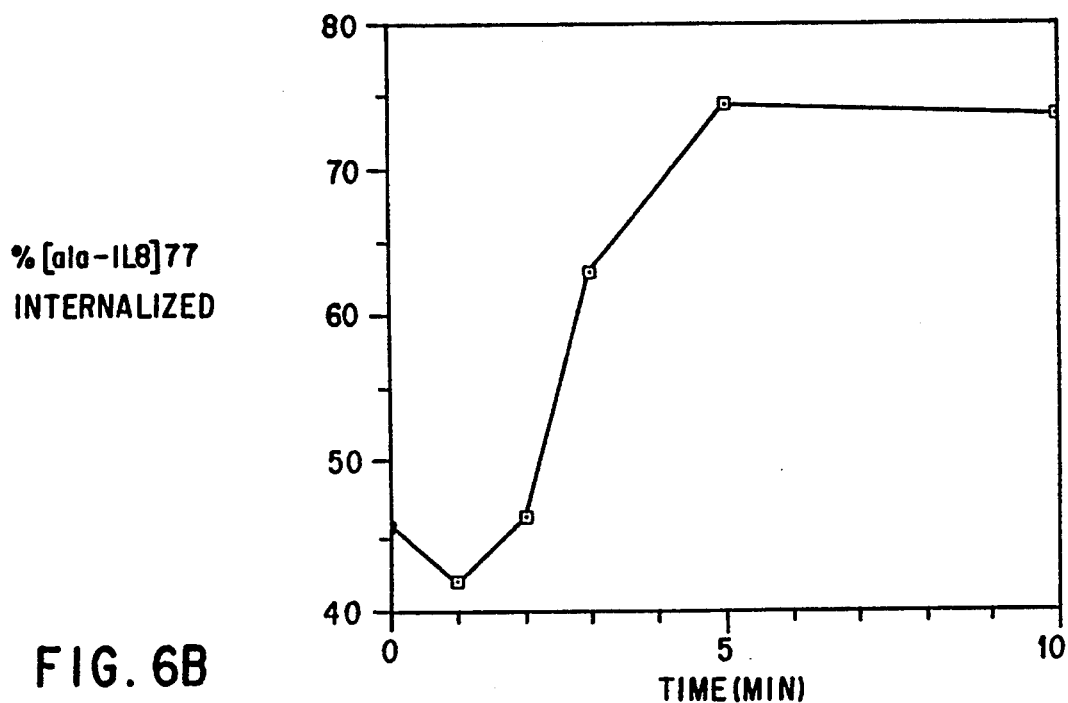
Figure 6C:
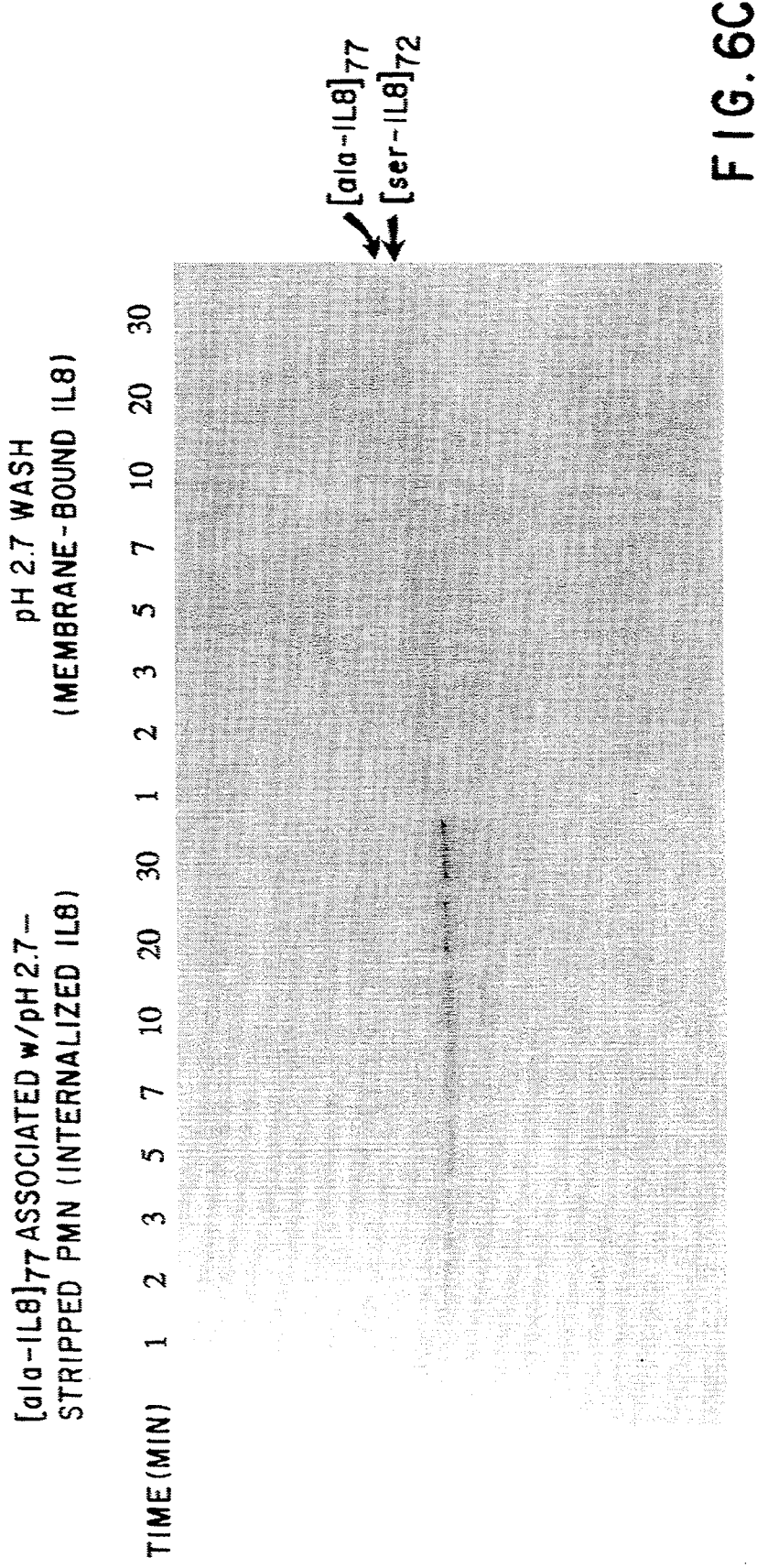

Internalization of the radioiodinated IL-8 ligand was monitored by determining the resistance of bound $^{125}$I-[Ala IL-8]$_{77}$ to extraction by pH 2.7 buffer at 4 C. for 10 min. FIG. 6A shows a time-dependant increase in total and acid extraction-resistant IL-8 associated with neutrophils. FIG. 6B shows that when the acid extraction-resistant IL-8 is expressed as % of total IL-8 bound to PMN, the data demonstrates a rapid internalization of IL-8, 75% of the total PMN associated IL-8 being internalized after 5 min. FIG. 6C shows that over the 30 min. time course of the binding incubation the acid extraction-resistant [Ala IL-8]$_{77}$ is converted to a species that comigrates with IL-8.

These data indicate that conversion of [Ala IL-8]$_{77}$ to a lower molecular weight IL-8 form, possibly IL-8, occurs concomitant with its uptake into neutrophils. This indicates that internalization may require cleavage of [Ala IL-8]$_{77}$. Hence, modified forms of [Ala IL-8]$_{77}$ that lack the arg cleavage site at position 5 may not be cleaved by neutrophils and therefore have increased half-lives in the bloodstream.

These data are also consistent with the possibility that Ala IL-8]$_{77}$ per se does not transduce signals to neutrophils. The biological activity of [Ala IL-8]$_{77}$ could depend on its conversion to IL-8 or (other lower molecular weight form). Hence, [Ala IL-8]$_{77}$ mutated to a noncleavable analog could have therapeutically valuable activity as IL-8 antagonist. This modification could be conversion of arginine at position 6 to an alanine residue, or other changes at other positions. Alternatively, segments of [Ala IL-8]$_{77}$ may find use as IL-8 antagonists.

EXAMPLE 13

In Vitro Activities of [Ala IL-8]$_{77}$ and IL-8. It was previously demonstrated that both HEC that have been activated with IL-1 and human 293 cells that have been transfected with an IL-8 -containing plasmid secreted two forms of IL-8, [Ala IL-8]$_{77}$ and IL-8, and that purified IL-8 preparations containing a mixture of these two forms inhibited neutrophil adhesion to cytokine-activated HEC monolayers. The LAI activity of each of the two IL-8 forms was tested in the in vitro LAI assay described above. Both forms of IL-8 were able to inhibit PMN adhesion by as much as 80% (FIG. 4). The maximally effective dose was about 1 nM in the case of IL-8 and 10 nM in the case of [Ala IL-8]$_{77}$. The EC$_{50}$ was about 0.3 nM in the case of IL-8 and about 2 nM in the case of [Ala IL-8]$_{77}$.

FIG. 8 shows that whereas [Ala IL-8]$_{77}$ and IL-8 both potentially inhibit the adhesion of neutrophils to IL-1-activated endothelium, these polypeptides do not detectably influence the interaction of monocytes or lymphocytes to this surface. Thus, these polypeptides potentially target neutrophils without inhibiting the immune functions of these other leukocytes.

FIG. 9 shows that [Ala IL-8]$_{77}$ markedly inhibits adhesion of neutrophils to endothelium that has been exposed to IL-1 for durations varying from 4 to 48 hours. This finding is significant because different types of endothelial receptors mediate adhesion during this time course (Luscinskas et al., *J. Immunol.* 142:2257 [1989]). Because [Ala IL-8]$_{77}$ inhibits PMN binding to activated endothelium mediated by more than one type of receptor system, compared to various anti-receptor monoclonal antibodies, [Ala IL-8]$_{77}$ has broader usefulness as inhibitor of neutrophil adhesion to vascular endothelium.

Although the foregoing invention has been described in some detail by way of illustration and example for purposes of clarity of understanding, it will be readily apparent to those of ordinary skill in the art of the teachings of this invention that certain changes and modifications may be made thereto without departing from the spirit or scope of the appended claims.

All publications and patent applications cited in this specification are herein incorporated by reference as if each individual publication or patent application were specifically and individually intended to be incorporated by reference.

What is claimed is:

1. A method of anti-inflammatory therapy comprising administering to a mammal in need of anti-inflammatory therapy a therapeutically effective amount of purified [Ala IL-8]$_{77}$ having leukocyte adhesion inhibition activity.

2. A method of treating inflammation in a mammal comprising administering a leukocyte adhesion inhibiting amount of purified [Ser IL-8]$_{72}$ having leukocyte adhesion inhibition activity.

3. The method according to claim 2, wherein said administering comprises injection into a site of inflammation.

* * * * *